(12) United States Patent
Izuchukwu

(10) Patent No.: US 7,438,072 B2
(45) Date of Patent: Oct. 21, 2008

(54) PORTABLE FIELD ANESTHESIA MACHINE AND CONTROL THEREFORE

(76) Inventor: John I. Izuchukwu, 18002 Pine Canyon Ct., Wildwood, MO (US) 63005

( * ) Notice: Subject to any disclaimer, the term of this patent is extended or adjusted under 35 U.S.C. 154(b) by 461 days.

(21) Appl. No.: 11/250,776

(22) Filed: Oct. 14, 2005

(65) Prior Publication Data
US 2006/0196505 A1    Sep. 7, 2006

Related U.S. Application Data

(60) Provisional application No. 60/657,983, filed on Mar. 2, 2005.

(51) Int. Cl.
*A61M 16/00*    (2006.01)
(52) U.S. Cl. .................... 128/203.15; 128/203.12; 128/204.14
(58) Field of Classification Search ............ 128/203.15, 128/203.12, 203.14, 203.25, 202.22, 204.14, 128/203.13
See application file for complete search history.

(56) References Cited

U.S. PATENT DOCUMENTS

| | | | |
|---|---|---|---|
| 3,021,840 A * | 2/1962 | Hallamore et al. ...... | 128/200.21 |
| 3,465,753 A * | 9/1969 | Levy et al. ............ | 128/203.14 |
| 3,814,092 A | 6/1974 | Simionescu et al. | |
| 4,034,753 A | 7/1977 | Connel | |
| 4,059,657 A | 11/1977 | Hay | |
| 4,129,621 A | 12/1978 | Jones et al. | |
| 4,150,670 A * | 4/1979 | Jewett et al. .......... | 128/204.22 |
| 4,770,168 A | 9/1988 | Rusz et al. | |
| 4,991,576 A | 2/1991 | Henkin et al. | |
| 5,146,915 A | 9/1992 | Montgomery | |
| 5,197,462 A | 3/1993 | Falb et al. | |
| 5,235,971 A | 8/1993 | Falb et al. | |
| 5,335,652 A | 8/1994 | Falb et al. | |
| 5,345,928 A | 9/1994 | Lindkvist | |
| 5,411,019 A | 5/1995 | Smith | |
| 5,419,316 A | 5/1995 | Bernstein | |
| 5,490,500 A | 2/1996 | Reichert et al. | |

(Continued)

OTHER PUBLICATIONS

International Search Report from corresponding International Application No. PCT/US06/07541, mailed Jan. 8, 2008.

(Continued)

*Primary Examiner*—Steven O Douglas
(74) *Attorney, Agent, or Firm*—Polster, Lieder, Woodruff & Lucchesi, L.C.

(57) ABSTRACT

A portable anesthetic machine comprises a chassis having a cradle which removably receives a vaporizer, a control panel and a support member. The control panel and support member are pivotal relative to each other to selectively change the machine between carrying and use configurations. The control panel includes a gas flow path having gas inputs connectable to sources of carrier gases, a manifold which combines the gases, a carrier gas outlet and inlet connectable to the vaporizer input and outlet, respectively, a common gas port, and flow control devices to control the carrier gas flow rate and to control the anesthetic and carrier gas mixture. A controller is also provided which controls the flow of gas into and around the vaporizer to maintain a substantially constant concentration of anesthetic agent in the gas stream delivered to the patient without the need to adjust the flow of gases from the gas supply sources.

25 Claims, 13 Drawing Sheets

U.S. PATENT DOCUMENTS

| | | | |
|---|---|---|---|
| 5,509,405 | A | 4/1996 | Mashak |
| 5,509,406 | A | 4/1996 | Kock et al. |
| 5,531,096 | A * | 7/1996 | Castor ..................... 73/23.2 |
| 5,535,737 | A | 7/1996 | Galbenu |
| 5,546,931 | A | 8/1996 | Rusz |
| 5,560,352 | A | 10/1996 | Heim et al. |
| 5,592,934 | A | 1/1997 | Thwaites |
| 5,664,561 | A | 9/1997 | Kersey |
| 5,673,688 | A | 10/1997 | Tham et al. |
| 5,778,874 | A | 7/1998 | Maguire et al. |
| 5,803,064 | A | 9/1998 | Phelph et al. |
| 5,806,513 | A | 9/1998 | Tham et al. |
| 5,810,001 | A | 9/1998 | Genga et al. |
| 5,890,908 | A | 4/1999 | Lampotang et al. |
| 5,957,129 | A | 9/1999 | Tham et al. |
| 6,021,777 | A | 2/2000 | Post et al. |
| 6,024,087 | A * | 2/2000 | Kersey et al. .......... 128/203.12 |
| 6,076,392 | A | 6/2000 | Drzewiecki |
| 6,536,430 | B1 | 3/2003 | Smith |
| 6,857,443 | B2 | 2/2005 | Volgyesi |
| 6,986,347 | B2 | 1/2006 | Hickle |
| 2003/0131844 | A1* | 7/2003 | Kumar et al. .......... 128/200.24 |
| 2004/0250813 | A1 | 12/2004 | Post et al. |
| 2004/0250814 | A1 | 12/2004 | Post et al. |
| 2006/0174889 | A1* | 8/2006 | Noble ................... 128/206.11 |

OTHER PUBLICATIONS

Written Opinion of the International Searching Authority from corresponding International Application No. PCT/US06/07541, mailed Jan. 8, 2008.

Gentilinnini A, Rossoni-Gerosa M, Frei CW, Wymann R, Morari M, Zbinden AM, et al. Modeling and Closed-loop Control of Hypnosis by Means of Bispectral Index (BIS) with Isoflurane. IEEE Trans Biomed Eng, Aug. 2001; vol. 48 No. (8): pp. 874-889.

Glass PS, Bloom M, Kearse L, Roscow C, Sebel P, Manberg P. "Bispectral analysis measures sedation and memory effects of propofol, midazolan, isoflurane, and alfentanil in healthy volunteers." Anesthesiology, Apr. 1997; vol. 86 No. (4): pp. 836-847.

Kenny GN, Mantzaridis H. "Closed-loop control of propofol anaesthesia." British J Anaesthesia 1999; vol. 83 No. (2): pp. 223-228.

Schuttler J, Schwilden H. "Present state of closed-loop drug delivery in anesthesia and intensive care." Acta Anesthesiol Belg 1999;50(4): 187-91 (Abstract).

Stephane Bibian, Craig R Ries, Mihai Huzmezan, Guy A. Dumont. Clinical Anesthesia and Control Engineering: Terminology, Concepts, Issues. European Control Conference, 2003; 1-11.

Michel MRF Struys, Tom De Smet, Eric P. Mortier. Closed Loop Anesthesia. Refresher Course. European Journal of Anesthesia, 2003: 9 RC 2:88-91.

Valerie Billard, "Bayesian forecasting and closed loop control of NMBA." Eurosiva, Nice 2002; 6 pages.

J. G. Bovill, "Targeting the effect site." Dept of Anaesthesiology, Leider University Medical Center; Leiden, The Netherlands—2 pages, printed Dec. 2004; http://www.eurosiva.org/Archive/Amsterdam/Abstractoral/Bovill.htmll.

Richard I. Cook, David D. Woods. "Implications of Automation Surprises in Aviation for the future of Total Intravenous Anesthesia (TIVA)." Journal of Clinical Anesthesia, 8:29S-37S, 1996.

D. A. Linkens, M. F. Abbod, M. Mahfouf. "An Initial Survey of Fuzzy Logic Monitoring and Control Utilisation In Medicine." Dept of Automatic Control and Systems Engineering, U. Sheffield, Sheffield, UK; 11 pages.

D. A. Linkens. "Fuzzy Control for Patient Muscle Relaxation." Dept. of Automatic Control and Systems Engineering, U. Sheffield, Sheffield, UK; 4 pages.

K. Ezra Kwok, Sirish L. Shah, Barry A. Finegan, Gary K. Kwong. "Experiences with Experimental Clinical Evaluation of a Computerized Drug Delivery System for Regulation of Mean Arterial Blood Pressure." 5 pages.

Ramesh R. Rao, Brian Aufderheide, B. Wayne Bequette. "Multiple Model Predictive Control of Hemodynamic Cariables: An Experimental Study."—Isermann Dept. of Chemical Engineering; Renssalaer Polytechnic Institute, Troy, NY—5 pages.

Ramesh R. Rao, Cesar C. Palerm, Brian Aufderheide, B. Wayne Bequette. "Experimental Studies on Automated Regulation of Hemodynamic Variables."—14 pages.

Ramesh R. Rao, B. Wayne Bequette, Rob J. Roy. Control of Hemodynamic and Anesthetic States in Critical Care Patients.; Depts. of Chemical and Biomedical Engineering; Rensselaer Polytechnic Institute, Troy, NY—6 pages.

Brett L. Moore, Eric D. Sinzinger, Todd M. Quasny, Larry D. Pyeatt. "Intelligent Control of Closed-Loop Sedation in Simulated ICU Patients." 2004, American Association for Artificial Intelligence.—6 pages.

A. Angel, R.H. Arbott, D.A. Linkens, C.H. Ting. "Somatosensory evoked potentials for closed-loop control of anaesthetic depth using propofol in the urethane-anaesthetized rat." Br. J. Anaesth 2000; 85: 431-9 http://bja.oujournals.org/cgi/content/ful/85/3/431.

T.J. Sieber, C.W. Frei, M. Derighetti, P. Feigenwinter, D. Leibundgut, A.M. Zbinden. "Model-based automatic feedback control versus human control of end-tidal isoflurane concentration using low-flow anaesthesia."—British J. Anaesthesia, 2000, vol. 85, No. 6—pp. 818-825.

Gavin NC Kenny. "Computer Delivery of Drugs."—Glasgow University Dept. of Anaesthetics, Glasgow, Scotland—Printed, Dec. 2004—3 pages.

James M. Bailey, Wassim M. Haddad, Tomohisa Hayakawa. "Closed-Loop Control in Clinical Pharmacology: Paradigms, Benefits, and Challenges." Proceedings of the 2004 American Control Conference, Boston, Massachusetts, Jun. 30-Jul. 2, 2004—pp. 2268-2277.

Michel M.R.F. Struys, Tom de Smet, Linda F.M. Versichelen, Stijn Van de Velde, Rudy Van Den Broecke, Eric P. Mortier. "Comparison of Closed-loop Controlled Administration of Propofol Using Bispectral Index as the Controlled Variable versus "Standard Practice" Controlled Administration." Anesthesiology vol. 95, No. 1, Jul. 2001—pp. 6-17.

Sebastian, A.A.P. Hoeksel, Johannes A. Blom, Jozef R.C. Jansen, Josephus G. Maessen, Jan J. Schreuder. "Automated infusion of vasoactive and inotropic drugs to control arterial and pulmonary pressures during cardiac surgery." Critical Care Medicine 1999; 27:2792-2798. http://www.sopami.hpg.ig.com.br/artigo14.htm.

Anthony R. Absalom, Nicholas Sutcliffe, Gavin N. Kenny. "Closed-loop Control of Anesthesia Using Bispectral Index." Anesthesiology, V 96, No. 1, Jan. 2002, 67-73.

A.R. Absalom, G.N.C. Kenny. "Closed-loop control of propofol anaesthesia using bispectral index: performance assessment in patients receiving computer-controlled propofol and manually controlled remifentanil infusions for minor surgery." British J. Anaesthesia, vol. 90 (6): 737-41 (2003).

R.J. Gajraj, M. Doi, H. Mantzaridis, G.N.C. Kenny. "Analysis of the EEG bispectrum, auditory evoked potentials and the EEG power spectrum during repeated transitions from consciousness to unconsciousness." British Journal Of Anaesthesia 1998; V. 80:46-52.

Michael Jastremski, et al. "A model for technology assessment as applied to closed loop infusion systems." Critical Care Medicine vol. 23, No. 10, Oct. 1995—pp. 1745-1758.

Michel M.R.F. Struys, Tom de Smet, Eric P. Mortier. Closed-loop control of anaesthesia. Modified from Current Opinion in Anaesthesia, 2002, 421-425—16 pages.

Mortier E., Struys M., Versichelen L., Rolly G., "Influence of infrared gas analysis of volatile anesthetics." Acta Anaesthesiol Belg. 1999; 50(3):119-23. (Abstract)—2 pages.

Michel M.R.F. Struys, Tom de Smet, Scott Greenwald, Anthony R. Absalom, Servaas Binge, Eric P. Mortier. "Performance Evaluation of Two Published Closed-loop Control Systems Using Bispectral Index Monitoring." Anesthesiology, Mar. 2004, V 100, No. 3,—pp. 640-647.

J.J. Ross, D.G. Mason, D.A. Linkens, N.D. Edwards. "Self-learning fuzzy logic control of muscular block." British Journal of Anaesthesia 1997; 78:412-415.

Stephen Locher, Konrad S. Stadler, Thomas Boehlen, Thomas Bouillon, Daniel Leibundgut, Peter M. Schumacher, Rolf Wymann, Alex M. Zbinden. "A New Closed-loop Control System for Isoflurane Using Bispectral Index Outperforms Manual Control." Anesthesiology, Sep. 2004; 101:591-602.

Schwildern H., Schutters, Stoeckel H., "Closed-loop feedback control of methohexital anesthesia by quantitative EEG analysis in humans." Anesthesiology, Sep. 1987; vol. 67 No. (3)—pp. 341-347 (Abstract)—2 pages.

* cited by examiner

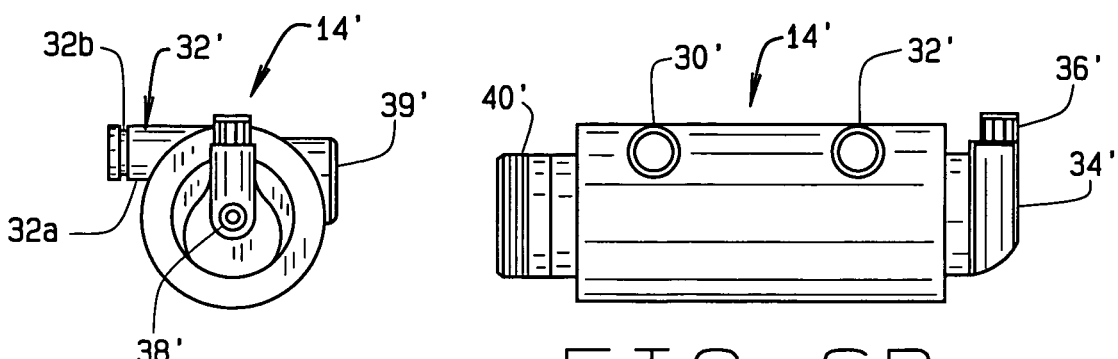
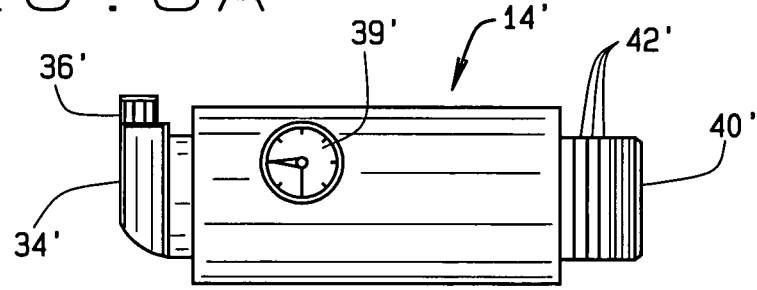
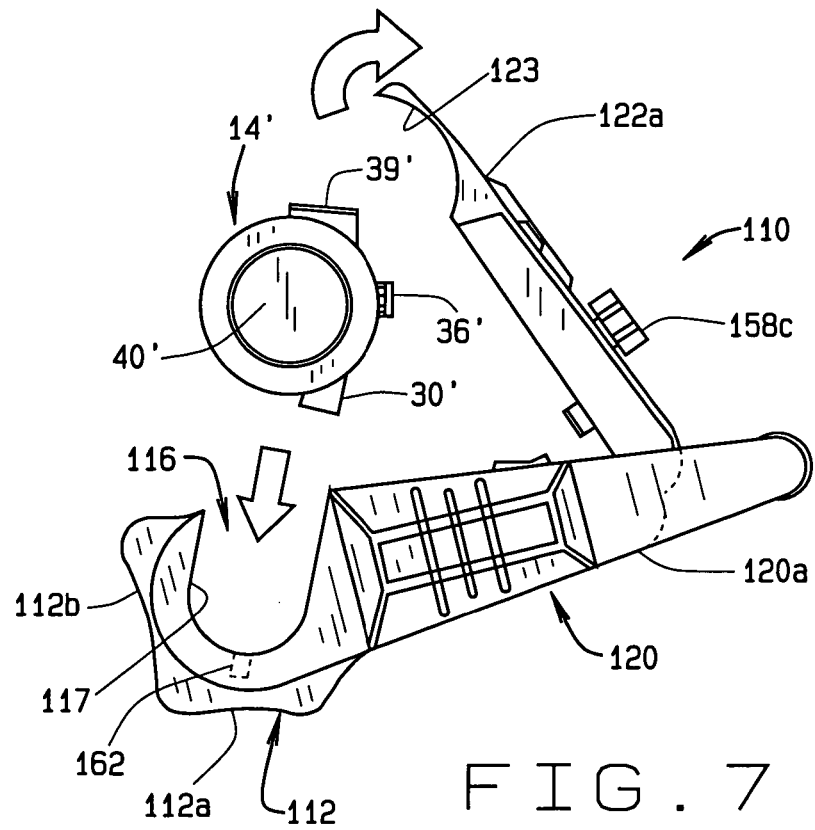

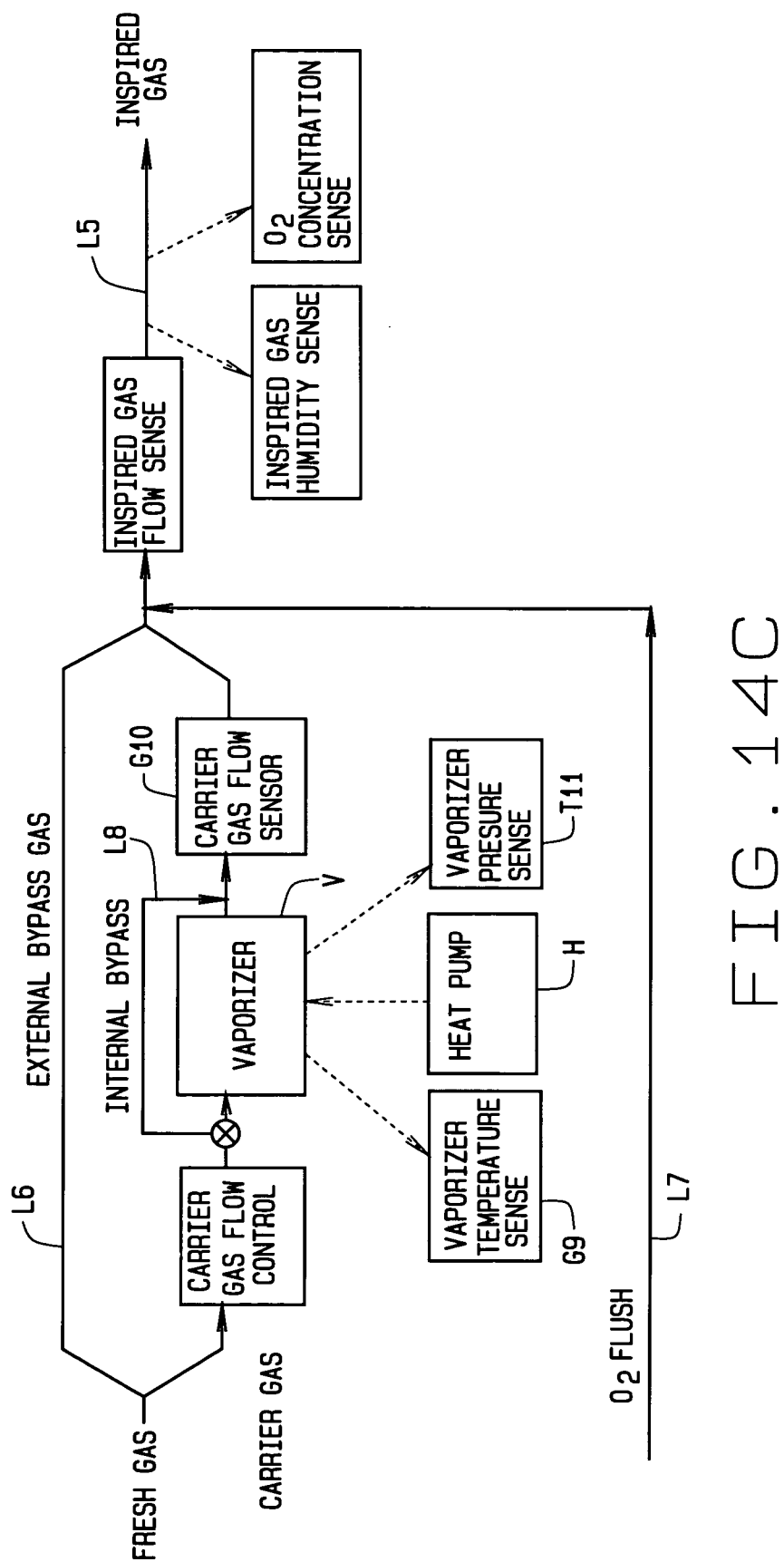

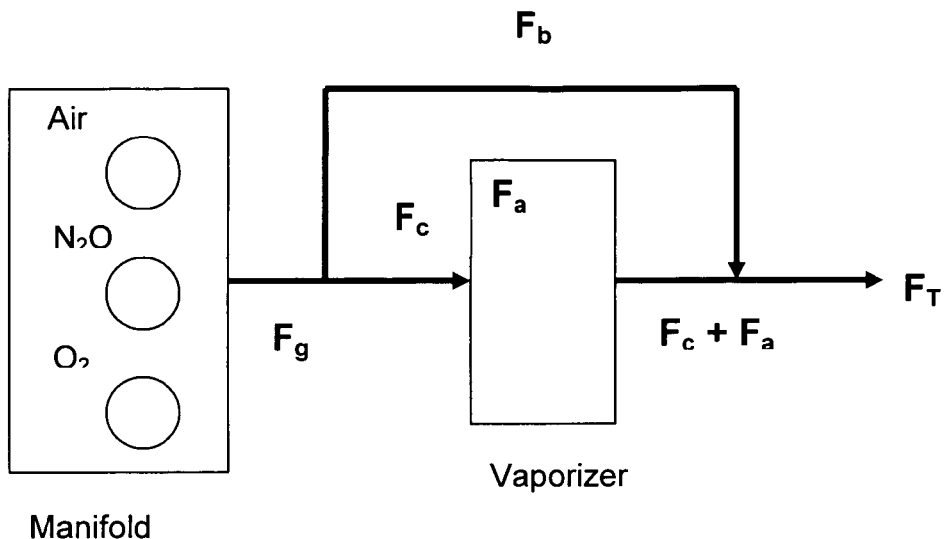
Figure 15: Gas Flows to and From Variable Bypass Vaporizer
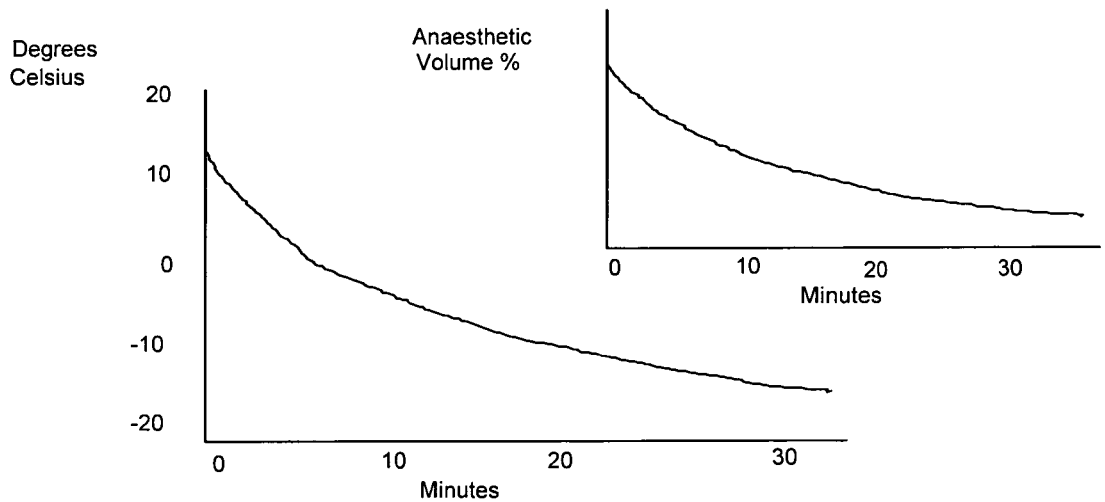
Figure 16: Vaporizer Thermodynamics (Temperature vs. Volume % Curves)

PORTABLE FIELD ANESTHESIA MACHINE AND CONTROL THEREFORE

CROSS-REFERENCE TO RELATED APPLICATIONS

This application claims priority to U.S. Provisional Application No. 60/657,983 filed Mar. 2, 2005, entitled "Portable Field Anesthesia Machine And Control Therefore", and which is incorporated herein by reference.

STATEMENT REGARDING FEDERALLY SPONSORED RESEARCH OR DEVELOPMENT

Not Applicable.

BACKGROUND OF THE INVENTION

This invention relates to anesthesia machines, and in particular, to anesthesia machines which are easily transportable.

Anesthesia machines are well known in the art for use in anesthetizing humans as well as other animals for surgical purposes. Virtually all prior art anesthetic machines are intended to be fixedly mounted in a stable environment, such as in a hospital operating room. This is usually required by the design of the machine and especially the vaporizer in which the liquid anesthetic agent is contained. Should the anesthetic machine be jostled, or its attitude be changed such as by tilting or the like, control of the rate of evaporation of the liquid anesthetic is affected and, in extreme cases of tilting or inversion, liquid agent may be directly introduced into the various passageways of the anesthesia machine such that the patient could be directly exposed to dangerous levels of the anesthetic agent. Such a circumstance could result in disastrous consequences.

When vaporizers are agitated or tipped more than 45 degrees from the vertical, liquid anesthetic is often discharged into the control mechanisms, obstructing valves. This results in the delivery of a large bolus of saturated vapor to the patient which could results in overdose. Other hazards have been reported involving calibrated vaporizers from several manufacturers. Displacement of liquid from a vaporizer to its outlet tubing can cause patient overdose, because not only the vaporizer flow, but total carrier gas flow then vaporizes the liquid anesthetic agent in an uncontrolled manner. Other known hazards include the possibility of using an incorrect agent in a vaporizer and some anesthesia machines are not compatible with MRI environments. They create artifacts that cause monitoring errors when used in these settings.

In addition, control of the delivery of anesthetic agents to patients when using both permanent and portable anesthetic machines can be improved upon. The two methods for controlling drug administration are open and closed-loop control. In open loop control, depth of anesthesia is regulated by adjusting a dial on the vaporizer to increase or decrease the concentration of the anesthetic gas delivered to a patient. This is the prevalent method today. Depth of anesthesia is observed by monitoring the patient's vital signs, using technologies that measure the patient's brain waves (electro-encephalogram), the heart's electric signals (electro-cardiogram), blood pressure and respiratory rate. Recent advances in closed-loop control of anesthesia have only focused on how to use these signals to control drug delivery.

Researchers caution that the results produced by controllers that depend on patient vital signs to regulate drug delivery to achieve depth of anesthesia, are unreliable and pose challenges because of the differences between patients. These patient dissimilarities have been attributed to genetic, enzymatic and metabolic differences. Recent articles attest that while measured values like blood pressure or muscular activity are direct indicators of the controlled variable, others like EEG are not. It is thus difficult to control the depth of anesthesia of a patient when a direct measurement of the drug effect is not possible.

No precedence exists for the application of closed-loop control to inhalation anesthetic vaporizers.

As is known, the vapor pressure of a gas is affected by variables such as temperature and pressure. As is also known, as the anesthetic in the vaporizer evaporates, the vaporizer chamber will cool, thus affecting the vapor pressure of the anesthetic agent and the amount of anesthetic agent that is entrained by the carrier gas. To maintain a proper amount of anesthetic agent, the flow rate of the carrier gas is typically adjusted at the inlet of the carrier gases to the anesthetic machine, and such adjustments are made manually. As can be appreciated, adjusting the flow rate of the individual gases which comprise the carrier gas can affect the overall composition of the carrier gas (i.e., the percentage of carrier gas made up of $O_2$, $N_2O$, and air. The manual modulation of gas flow rates to compensate for decline in anesthetic concentration due to cooling, or changes in barometric pressure, to maintain anesthetic depth is a tedious and unreliable process, because of the time difference between the observed physiologic signal and the physician response. The challenges of mechanical control of vaporizer performance, necessitates an evolution to electromechanical control, integrating a degree of intelligence not found in any vaporizer in commercial existence, to achieve consistent precision and reliability. Such a vaporizer will pave the way for a new class of field anesthesia machines.

While the hazards of existing vaporizers are known and safety recommendations have been published only a partial solution has been attempted by manufacturers, which is aimed at their traditional hospital based business. This includes precision vaporizers that can only be used with one agent. Precision vaporizers by design are agent-specific and utilize indexed funnels to prevent accidental filling with the wrong agent. This means that healthcare providers must purchase multiple vaporizers (one per agent), which is cost prohibitive in an era of cost containments and reimbursement cuts. Existing anesthesia machines which incorporate traditional vaporizers are not suitable for ambulatory applications because of their sensitivity to orientation, shock and vibration, as would be encountered in the field, and are worsened by their dependence on availability of compressed gas and electricity to operate. In addition, they are bulky, heavy, and complex to setup and maintain, and require tremendous logistical overhead to transport. There is no transportable anesthesia machine that is designed specifically for field applications, and in particular non-traditional surgical environments.

Military and civilian doctors have expressed a need for transportable anesthesia machines with reduced logistics footprint, to facilitate far-forward surgical care in combat and non-traditional operating environments. Unlike previous anesthesia machines, it would be one-man transportable, reliable, simple, tippable, insensitive to shock and vibration, and vagaries of weather, does not require compressed gas, easy to setup, use and maintain, and compatible with standard off-the-shelf physiologic monitors and portable ventilators. Transportable anesthesia machines would also be of use to disaster care organizations and humanitarian care organizations, such as FEMA (Federal Emergency Management Agency), Doctors Without Borders, Wings Of Hope, Red Cross, etc., for mass civilian casualty care and surgery in third world settings.

Such anesthesia machines will help to perform life resuscitative surgery in the battlefield, "to extend the 'golden hour' for treatment, in order to improve survival rate from life threatening injuries, including those from improvised explosives, and minimize morbidity after other life-threatening injuries". These technologies will improve the first responder's capability to provide effective treatment more rapidly and as close to the place of the injury as possible. Furthermore, they will be of immense utility during peace keeping and post-war or post-disaster reconstructive initiatives around the world. "Without the appropriate equipment, management of the seriously injured patient is impossible for even the most competent anesthetist."

Today's medical equipment and in particular general anesthesia machines are not suitable for the delivery of critical medical care or emergency surgery in less than ideal terrains or environments. The answer is not expensive medical devices but practical and reliable equipment, designed for the surgical conditions encountered in the field. It has long been recognized by physicians practicing in the field that the essentials for safe anesthesia in any situation does not depend on expensive equipment but safe anesthesia induction, a secure airway, adequate tissue oxygenation, appropriate monitoring and recovery. This is reinforced by the fact that in many parts of the world resources are scarce, and even a regular supply of compressed gases such as nitrous oxide and oxygen is not possible. This poses a major challenge for anesthesiologists working in these environments.

Portable anesthesia machines could be used in the field, or in combat-surport hospitals, to stabilize patients prior to transporting the patients to full service hospitals. Surgical care in the field is limited logistically by the size, weight, complexity and sensitivity of traditional anesthesia machines to environmental conditions. Currently, field hospitals must carefully transport, and then set up, these anesthesia machines. Such a system is not feasible when the machine is to be used at a locale for only a short period of time. In addition, small clinics serving patients in third world countries typically cannot afford an anesthesia machine. Hence it would be desirable to have such a machine which is easily transportable to allow two or more clinics to share one machine, and to move the anesthetic machine between the clinics as needed. Because such clinics generally cannot afford, and hence do not have, anesthesia machines, any patient requiring even minor surgery must be transported at great difficulty to the nearest city having a hospital or clinic with an anesthetic machine. It would be desirable to provide an anesthesia machine which could be used in such situations.

An historical approach to overcoming the shortage or absence of compressed gas is the use of a draw over vaporizer, which works in an open circuit mode, similar to the Oxford Miniature Vaporizer. Draw over systems are designed to provide anesthesia without requiring a supply of compressed gases. Atmospheric air is used as the main carrier gas and is drawn by the patient's respiratory effort through the vaporizer, containing the volatile anesthetic agent. The mixture is then inhaled by the patient through a non-rebreathing valve. These types of vaporizers typically have low internal resistance, and the volume of air passing through the vaporizer is determined by the patient's tidal volume (the volume of air in a single breath) and the respiratory rate.

The machines now used for combat casualty care, such as the NarcomedM, Ohmeda 885A and the Oceanic Magellan are too big and complex, require compressed gas and electricity, plus battery backup, extensive setup time, and logistical overhead to deploy. The NarcomedM from Datex Ohmeda for example weighs 163 pounds and requires two men to transport.

For decades, there has been a continual increase in the number of surgeries performed on an outpatient basis and in the field, yet anesthesia machines have not advanced to address the unique requirements of inhalation anesthesia induction in these environments, such as reduced footprint and weight, and reliability in extreme environmental conditions, outside of the traditional operating rooms, from private physician clinics to the far-forward location of the battlefield and third world settings. They are bulky and cannot be transported by a single medic or first responder on foot, and depend on an agent specific vaporizer which necessitates the transport of multiple vaporizers, for different anesthetic agents; escalating the weight penalty and logistics burden. Furthermore, they require infrastructure that are often not available in the environment. Because of their sensitivity to orientation and vibration, they cannot be used without recalibration if tipped or jolted, making them unsuitable for surgical applications in a theater that is susceptible to vibration, such as a war zone, or moving medical transport vehicle.

In the asymmetric warfare of the $21^{st}$ century where soldiers can be attacked and wounded anywhere, medical teams must be agile and able to work as close as possible to the battlefield. The potential escalation of casualties in this type of warfare due to weapons of mass destruction and improvised explosive devices, in unexpected areas, including alleys, underscores a need for medical personnel to be able to perform life resuscitative surgery anywhere. This is reinforced by the likelihood that a medical evacuation vehicle while on-route to retrieve wounded soldiers, may be destroyed and thus fails to deliver medical assistance within the golden hour.

BRIEF SUMMARY OF THE INVENTION

An anesthetic delivery machine of the present invention overcomes many of the drawbacks of traditional machines. In accordance with one aspect, the machine can be used in plenum or draw-over mode, and does not require electricity to deliver the anesthetic agent to the patient.

This device will facilitate casualty care in military and civilian environments, and enable surgery to be performed in private physician clinics, as well as rural and remote hospital settings around the world. In accordance with one aspect, it is small enough and light enough to be transported in a briefcase, backpack or wheeled container, fully charged with anesthetic, ready for deployment in emergency situations, such as civilian and combat casualty care.

In accordance with an aspect the anesthetic machine delivers precise concentration of anesthetics, regardless of environmental temperature and pressure; and is capable of sensing and compensating for the changes in temperature and pressure in order to maintain accurate anesthetic gas concentration.

In accordance with a further aspect, the anesthetic delivery machine is orientation insensitive, does not require compressed gas or electricity to deliver anesthetic gas, and will substantially maintain the anesthetic gas concentration delivered to the patient when exposed to shock and vibration, disorientation or agitation without loss of calibration or discharge of anesthetics into the patient's airway. The machine is switch selectable from plenum to draw-over mode for when compressed gas has been exhausted, or when there is no compressed gas. Thus, in drawover mode, the machine will possess minimum internal resistance to enable induction by a patient's tidal volume so that the device can be used in surgical environments where compressed gas is not available. The machine is substantially insensitive to shock and vibration. It automatically controls the variables that affect vaporizer output and accuracy to minimize the dangers of manual compensation and constant vigilance by operators in order to maintain the depth of a patient's sedation. This anesthesia delivery machine is substantially lighter than the smallest anesthetic delivery machines presently in the market. Furthermore, the machine requires significantly less time to setup and overhead to maintain.

An anesthesia delivery machine made in accordance with the present invention can include one or more of the following features:

A vaporizer removably receivable in a carriage of a control unit, the control unit embodying a controller, thermal and pressure sensors, actuators, proportional and variable aperture valves or solenoid valves for regulating carrier gas flow rate, monitoring thermal and pressure gradients and controlling the vapor pressure of anesthetics.

The vaporizer has a gas-inlet and gas outlet and a reservoir for an anesthetic agent in communication with the inlet and flow path of the carrier gas as well as a reservoir funnel.

A one-way valve enables unidirectional carrier gas flow from a manifold into the vaporizer, and an actuator controls the aperture of the valve, when signaled by the controller to increase or decrease the carrier gas flow rate, in order to achieve a desired gaseous mixture and anesthetic concentration.

The vaporizer can include a stoichiometry analyzer, which, based on the density, specific heat or vapor pressure of the anesthetic, determines the anesthetic content of the vaporizer.

The vaporizer can include a detector which determines the anesthetic agent in the vaporizer and an interface or monitor which indicates (for example by displaying the color code, agent, name, or chemical symbol of the anesthetic agent) the agent contained within the vaporizer. The anesthetic agent identifying display can, for example, be an analog or digital display.

The device can include sensors which detect changes in temperature and barometric pressure that are coupled to a feedback system that compares the changes against a reference template of standard temperature and pressure at sea level to determine the degree of compensation needed.

The device can include a mechanical or digital interface to an anesthesia machine to display anesthetic agent concentration, using refractive indices of the anesthetics and methods of gas analyses, as well as to display vapor pressure in relationship to the content of the vaporizer on a vapor pressure gauge.

The device can include a heating and cooling mechanism, such as an thermoelectric heat pump (such as a peltier-junction), which compensates for changes in temperature by addition or withdrawal of heat to maintain the temperature of that vaporizer chamber at a desired temperature (such as about 20-25° C.), or a metallic strip that acts as a heat sink to prevent heat loss by redirecting the heat of vaporization into the anesthetic.

The device can include an internal and external pressure gauge or sensor with feedback mechanism to the controller which compensates for pressure variations due to changes in altitude, by regulating the heat input or carrier gas flow rate to achieve and maintain dialed concentration.

The vaporizer can include a dial for selecting a set concentration mechanically, or by means of a numerical key pad that is linked to a controller which stores the pre-selected value in ROM memory.

The vaporizer can include a visible indicator, to display the vapor pressure and concentration of anesthetic in the vaporizer outlet versus the set concentration.

The device can include a control algorithm that uses the values from the sensors as a template to determine deviation from target temperature and pressure and to signal compensation.

The device can include a switch selectable feature on the vaporizer which enables it to be used in closed circuit, open or out of the circuit mode by varying the diameter of the vapor flow channels to reduce inspiratory resistance.

The device can include a pressure sensor within the wall of the vaporizer for communicating the dynamic pressure (vapor pressure) within the cylinder to an analog or digital device on the vaporizer enclosure or anesthesia machine. The interface between the sensors and the microcontroller can comprise 8 or more channels of 10-bit analog to digital input, capable of handling a minimum of 100 data samples per second, with 8 channels of 1-bit digital control output that may be pulse-width modulated, and full-duplex RS232 data port to a PDA host, other portable computing device or monitor. A data recording device, with real-time-clock/date for tracking usage statistics and vaporizer settings versus output, as well as temperature and pressure The vaporizer can be sleeved circumferentially by a layer of shock absorbing and high durometer rubber, to make it insensitive to shock and vibration. Such a sleeve will also serve as a thermal shield to prevent heat loss and heat gain between its wall and the outside.

The vaporizer can contain a pair of one-way poppet valves, located on its body which serves as carrier gas inlet and an outlet for the carrier gas/anesthetic gas mixture, respectively.

The device can include an anesthetic agent identification system. The anesthetic agent identification can be accomplished by means of infrared spectroscopy (volatile anesthetic agents absorb infrared light), refractometry (using the refractive index of the agent). electrochemical sensors, color change chemistry, ion mobility spectroscopy, mass spectrometry, Raman spectroscopy, gas chromatography, density and molecular weight. The infrared region of the electromagnetic spectrum, which is between 2.5 and 25 micrometers has been proven valuable in chemistry and physics for the identification and quantification of gaseous molecules. When infrared radiation passes through a gas, absorption of radiation occurs at specific wavelengths that are characteristic of the vibrational structure of the gas molecules. In the case of anesthetic agents, there are several absorption peaks that can be used, 10-13 mm being a common range of wavelengths. Light in this wavelength range is shone through a gas sample and the absorption is proportional to the anesthetic vapor concentration. Absorption at other wavelengths may also be measured so that the agent being used can be identified automatically. One problem with these monitors for veterinary use is that methane produced by ruminants can interfere with the measurements. Electrochemical sensors quantify the interaction between an analyte's (i.e., the agent's) molecular chemistry and the properties of an electrical circuit. It is based on the chemical reaction that occurs when the anesthetic agent enters the detection region and a change in the electrical potential occurs. This change is normally monitored with an electrode. It requires a threshold concentration which corresponds to a change in the monitored electrical potential. Color change chemistry is based upon chemical reactions that occur when agents interact with various solutions and substrates. The most common indicator for a positive reaction is a color change. Raman spectroscopy is based upon the observation that when radiation is passed through a transparent medium, chemical species present in that medium scatter a portion of the radiation beam in different directions. The wavelength of a very small fraction of the radiation scattered differs from that of the incident beam. The difference between the scattered radiation and incident beam corresponds to wavelengths in the mid-infrared region. The degree of wavelength shift is dependent upon the chemical structure of the molecules causing the scattering. During irradiation the spectrum of the scattered radiation is measured with a spectrometer. In the case of mass spectrometry, ions of the anesthetic gas molecules are separated by the mass analyzer, and measure the mass to charge ratio of the ions. This technique only requires a very minute sample to obtain characteristic information regarding the structure and molecular weight of the analyte (agent). Gas chromatography can be also used to detect the type of anesthetic agent. After subjected a sample to a volatile solvent extractor, a small sample of the mixture is injected into a heated injection port that vaporizes the sample, which is swept into a column by the inert carrier gas. After passing through the column the solute of interest generates a signal for a recording device to read

BRIEF DESCRIPTION OF THE SEVERAL VIEWS OF THE DRAWINGS

FIG. 6A-C are end, front and back elevational views of a second embodiment of a vaporizer for use with the anesthetic machine of the present invention;

FIG. 7 is a side elevational view of a second embodiment of an anesthetic machine of the present invention, the anesthetic machine being shown in an open position to receive a vaporizer;

FIG. 15 is a block diagram of the gas flow to, and by pass around, the vaporizer; and FIG. 16 are vaporizer thermodynamics charts on which temperature vs. % anesthetic concentration over time is illustrated for a traditional vaporizer.

Corresponding reference numerals will be used throughout the several figures of the drawings.

DETAILED DESCRIPTION OF THE INVENTION

Figure 1:
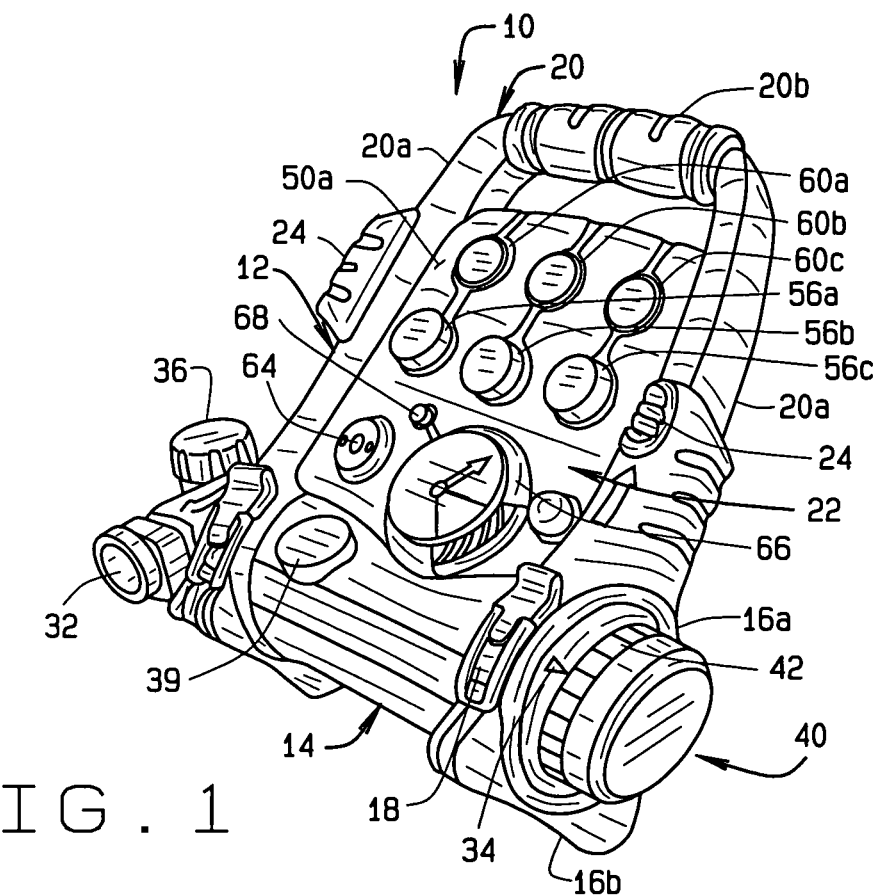
FIG. 1 is a front perspective view of a first illustrative embodiment of an anesthetic machine of the present invention.

The following detailed description illustrates the invention by way of example and not by way of limitation. This description will clearly enable one skilled in the art to make and use the invention, and describes several embodiments, adaptations, variations, alternatives and uses of the invention, including what I presently believe is the best mode of carrying out the invention. Additionally, it is to be understood that the invention is not limited in its application to the details of construction and the arrangements of components set forth in the following description or illustrated in the drawings. The invention is capable of other embodiments and of being practiced or being carried out in various ways. Also, it is to be understood that the phraseology and terminology used herein is for the purpose of description and should not be regarded as limiting.

Figure 2:
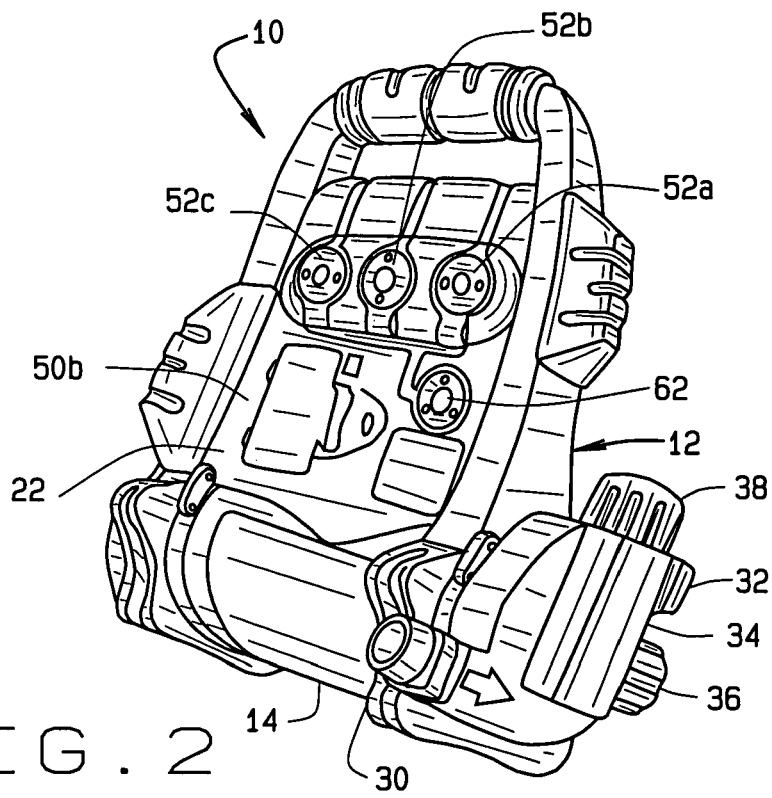
FIG. 2 is a rear perspective view of the anesthetic machine.
Figure 3:
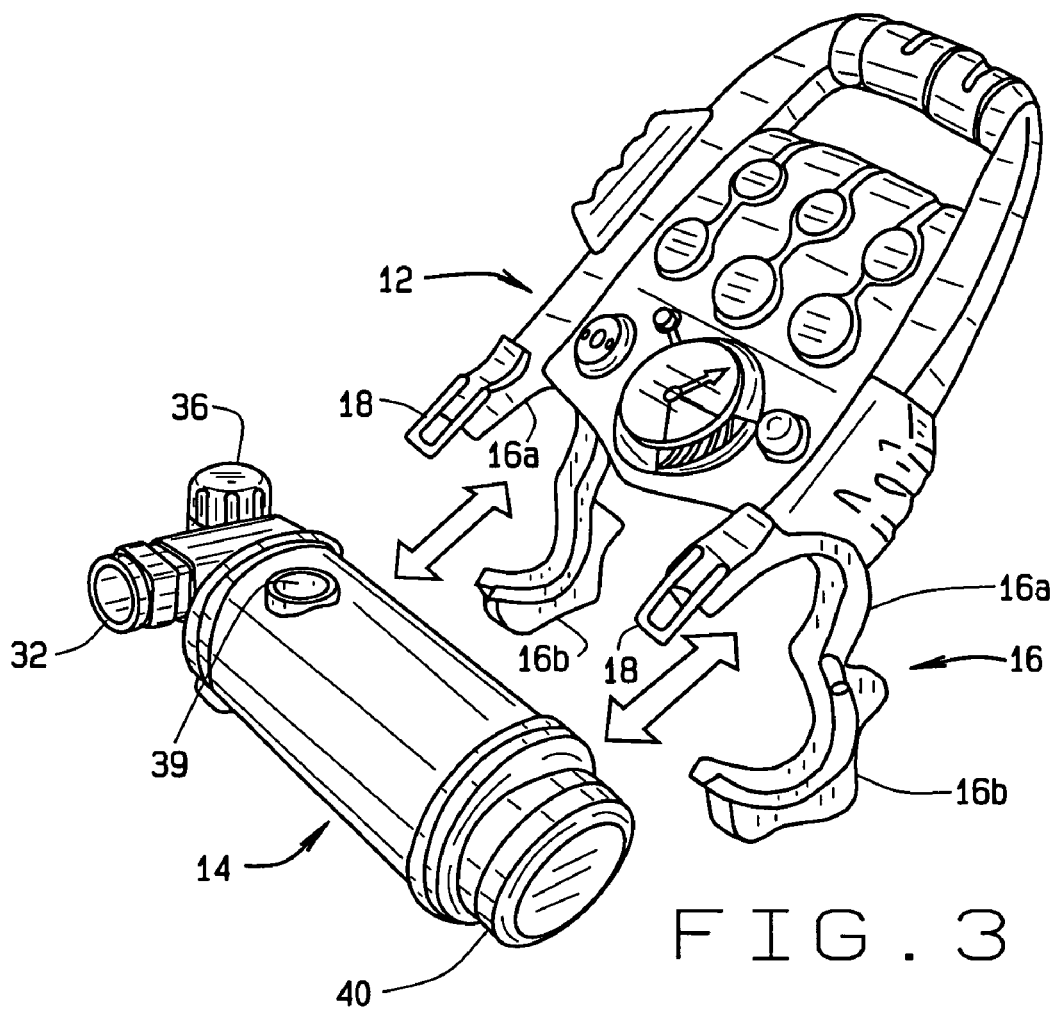
FIG. 3 is an exploded view of the anesthetic machine showing the ability to remove the vaporizer from the machine chassis or carriage.

An illustrative first embodiment of an anesthetic machine 10 of the present invention is shown generally in FIGS. 1-3. The anesthetic machine 10 comprises a chassis 12 which removably receives a vaporizer 14. As seen best in FIG. 3, the chassis 12 includes, at the bottom thereof, a cradle 16 in the form of a clasp or clamp comprising a fixed portion 16a and a movable portion 16b hingedly connected to the fixed portion at one end thereof. The fixed and movable portions of the clasp included matable latches 18 at their free ends which cooperate with each other to maintain the clasp portions together to thereby hold the vaporizer 14 to the chassis 12. The clasp latches 18 can be opened to allow for the vaporizer to be removed from the chassis.

A generally U-shaped handle 20 extends upwardly from the chassis. The handle 20 includes arms 20a extending upwardly from the clasp fixed portion 16a and a gripping portion 20b extends between the arms 20a at the tops thereof. A panel 22 is between the arms 20a of the handle. As will become apparent below, the panel 22 forms a body for the anesthetic machine. The handle arms 20a are sized such that there is a space between the handle gripping portion 20b and the top of the panel 22, to enable an operator to easily grasp the handle gripping portion to lift and carry the anesthetic machine 10.

Figure 5A:
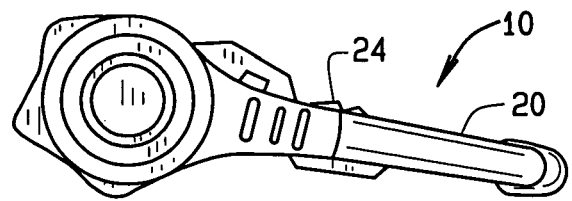
FIGS. 5A-D are side elevational views showing the deployment of the anesthetic machine.
Figure 5B:
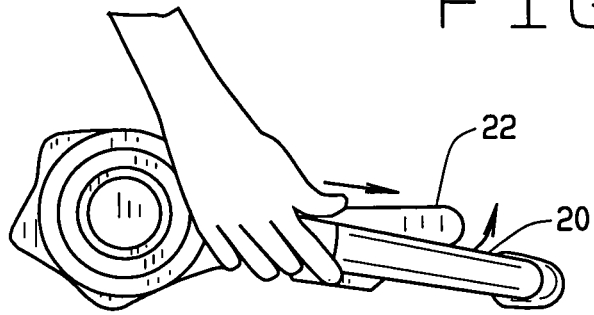
Figure 5C:
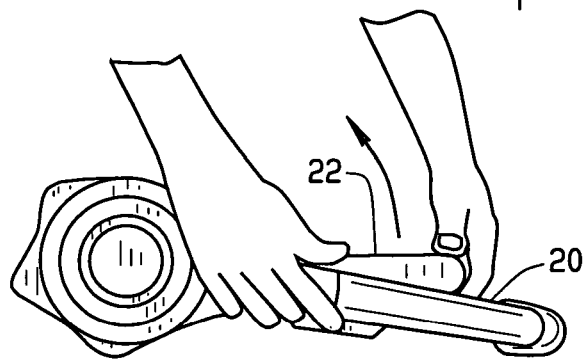
Figure 5D:
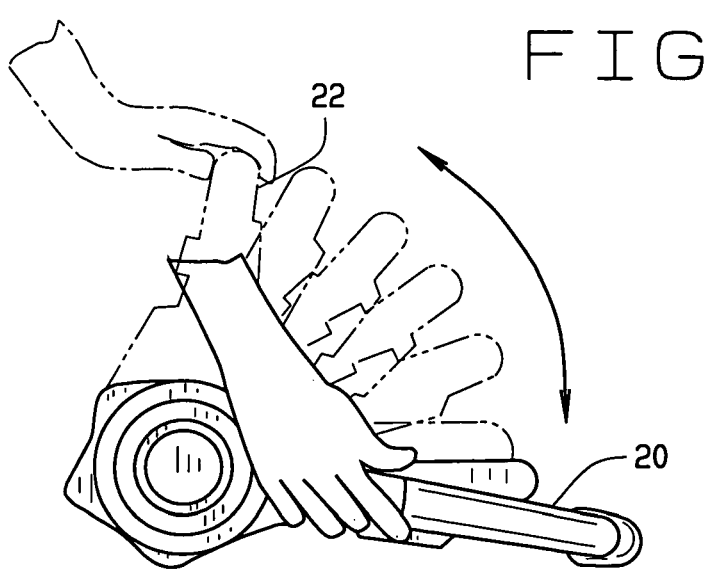

The panel 22 is pivotally connected to the handle arms 20a, such that the panel 22 can, as seen in FIGS. 5A-D, pivot or articulate relative to the handle 20. The panel 22 can be locked relative to the handle, such that the panel will not pivot out of a desired position. The handle 20 includes slides or levers 24 which when pressed, release the locking mechanism to allow the panel to be pivoted relative to the handle. Hence, the panel 22 and handle 20 can be pivoted relative to each other from a carrying position (as seen in FIG. 1) in which the panel 22 and handle 20 are essentially co-planar, and a use position, as seen in FIG. 5D, in which the panel 22 is angled relative to the handle 20, and the handle 20 supports the panel in an elevated position. As can be appreciated, in this use position, the handle 20 defines a base for the machine 10. Detent, ratcheting or spring biased mechanisms within the base of the handle arms 20a and the panel 22, enables angular adjustment of anesthesia machine housing and gauges, relative to the handle to stabilize the machine as well as to provide a good monitoring angle for the physician. The slides 24 serve as a lock and release mechanism, while the detents, pivoting, articulating and ratcheting mechanisms control the degree of tilt.

The vaporizer 14 (FIGS. 3 and 4) includes an inlet 30 to receive carrier gas and an outlet 32. A chamber 34 receives the anesthetic agent and is accessed through a funnel covered with a cap 36. A second cap 38 is provided to drain the chamber 64 of anesthetic agent when necessary. A level gauge 39 is provided to allow the practitioner/user to determine the amount of anesthetic agent remaining in the vaporizer. A control dial 40 is provided at the opposite end of the vaporizer from the chamber 38. The control dial 40 is used to set the vapor pressure of the anesthetic agent to be delivered to the patient. To this end, the control dial 40 includes indicia 42 which, when aligned with a second indicia 34 (shown as an arrow) informs the operator of the percentage of anesthetic agent in the exiting gas stream. The indicia can be formed on or comprise color coded bands of concentric marks and numerals, for selecting a desired concentration of a specific anesthetic agent. Each color band corresponds to the industry standard for a specific agent color. The indicia 42 preferably indicate the percentage of anesthetic agent that will make up the gas delivered to the patient. Typically, the indicia 42 are calibrated for standard pressure and temperature (i.e., about 760 mmHg and about 20-25° C.). The basic operation of the vaporizer 14 and the dial 40 is well known in the art, and is not described herein.

Turning to FIGS. 1 and 2, the panel 22 includes a front surface 50a and a back surface 50b. The panel includes ports 52a-c on the panel back side 50b which receive hoses from supplies of air, $N_2O$ and $O_2$, respectively. The air supply source can, for example, be either a canister or tank of compressed air or a compressor. The $N_2O$ and $O_2$ can be supplied by tanks of compressed gas. The $O_2$, alternatively, can be supplied by an oxygen concentrator. Dials 56a-c on the panel front surface 50a are used to operate valves to control the flow rate of the gases into the anesthesia machine 10. Pressure gauges 60a-c are provided to enable the operator to monitor the flow of the respective gases into the anesthesia machine 10.

The three gases are combined in a manifold M (FIG. 14) to form a carrier gas. It will be appreciated that the carrier gas can comprise one or more gases, for example, a physician may use only air as the carrier gas. This carrier gas is directed to a carrier gas outlet 62 on the panel back surface 50b which is connected to the vaporizer inlet 30. The vaporizer outlet 32, in turn, is connected to a common gas inlet 64 is on the panel front surface 50a. The connections between the common gas outlet and the vaporizer inlet and between the vaporizer outlet and the common gas inlet can be made, for example, by removable tubing. As can be appreciated, after the gas passes through the manifold M, the carrier gas is directed to the vaporizer 14 through the panel outlet 62 and the vaporizer inlet 30. In the vaporizer, the carrier gas entrains vaporized anesthetic agent and exits the vaporizer through outlet 64. The carrier gas with entrained anesthetic agent then re-enters the panel through the common gas inlet 64. A circuit pressure gauge 66 on the panel front displays the line pressure of the entering carrier gas. A gas outlet 68 receives tubing to deliver the gas to the patient. Lastly, an $O_2$ push button 70 on the surface 30a operates a valve which provides a burst of oxygen to the patient, should the operator believe such is needed. As described below, $O_2$ delivered in response to the pressing of the $O_2$ push button will bypass the vaporizer and other gas paths, and be delivered directly to the patient.

The anesthetic machine can be provided with a breathing circuit 72 (FIG. 14) which is positioned between the common gas outlet 68 and the cannula which delivers the gas to the patient. The breathing circuit includes a Y-junction 74 which separates the breathing circuit into an inhalation branch 76 and an exhalation branch 78 of the breathing circuit. The exhalation branch 78 carries exhalation gases from the patient toward the Y-junction. Such exhalation gases include air, nitrogen, $O_2$, $CO_2$, other trace elements present in the inhaled air, as well as anesthetic agents. A $CO_2$ scrubber 80 is inserted in the exhalation branch to remove the $CO_2$ from the gas stream. After the CO2 content of the exhaled gas is removed by the scrubber 80, the remaining gases in the exhalation branch are united or mixed with the gases in the inhalation branch to deliver to the patient a combination of the scrubbed anesthetic agent from the exhalation branch with fresh anesthetic gas from the vaporizer.

Figure 4:
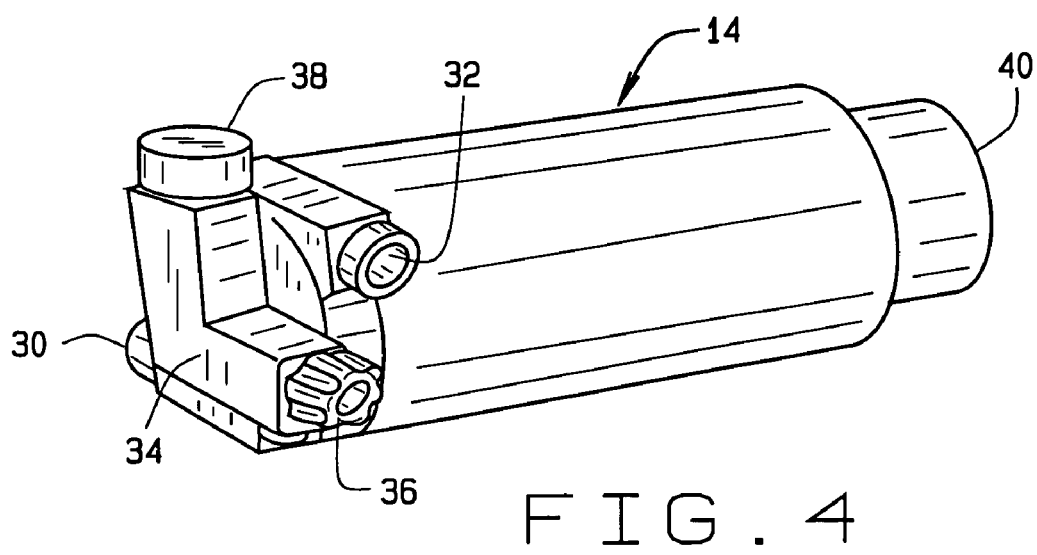
FIG. 4 is a perspective view of an illustrative embodiment of a vaporizer for use with the anesthetic machine of the present invention.

In FIGS. 6A-C, a second alternative embodiment of the vaporizer is shown. The vaporizer 14' is substantially similar to the vaporizer 14 (FIG. 4). However, rather having the gas inlet and gas outlet at an end of the vaporizer, the vaporizer 14' includes an inlet 30' and an outlet 32' along its side surface. The inlet 30 and outlet 32 of the vaporizer 14 are connected to the gas ports 62 and 64 via tubing (which is not shown in FIGS. 1 or 2). By placing the vaporizer's inlet 30' and outlet 32' on the side of the vaporizer, the vaporizer's inlet and outlet can be directly mated or connected to corresponding ports in the vaporizer cradle of the anesthesia machine. This eliminates the need for additional tubing, and reduces the time involved in setting up the anesthesia machine.

As best seen in FIG. 6A, the outlet 32' (the inlet 30' being identical thereto) comprises a tube 32a which extends outwardly from the vaporizer body. The tube 32a is provided with a groove 32b near its free end to accept an O-ring. This O-ring will form a fluid tight seal between the tube 32 and the port in the anesthesia machine which receives the tube 32a.

As with the vaporizer 14, the vaporizer 14' includes a fill tube or chamber 34' having a cap 36'. A drain 38' is provided to empty the chamber 34' of any remaining anesthetic agent at the end of a procedure. The vaporizer also includes a level gauge 39' to monitor the level of anesthetic agent within the vaporizer and a control dial or knob 40' to set the vapor pressure of the anesthetic agent to be delivered to the patient. The control dial 40' includes indicia 42' which, when aligned with a second indicia informs the operator of the percentage of anesthetic agent in the exiting gas stream. The indicia 42 preferably indicate the percentage of anesthetic agent that will make up the gas delivered to the patient. The vaporizer 14 included a single set of indicia 42. The dial 40' of vaporizer 14' however, is provided with three sets of indicia 42' which are color coded to correspond to commonly used anesthetic agents. Hence, the vaporizer 14' is precalibrated for use with different anesthetic agents. By precalibrating the vaporizer for different anesthetic agents, the vaporizer can more easily be used with different anesthetic agent. Preferably, the vaporizer would be precalibrated with more commonly used anesthetic agents, such as Halothane, Ethrane, Isoflurane and Sevoflurane.

Figure 8:
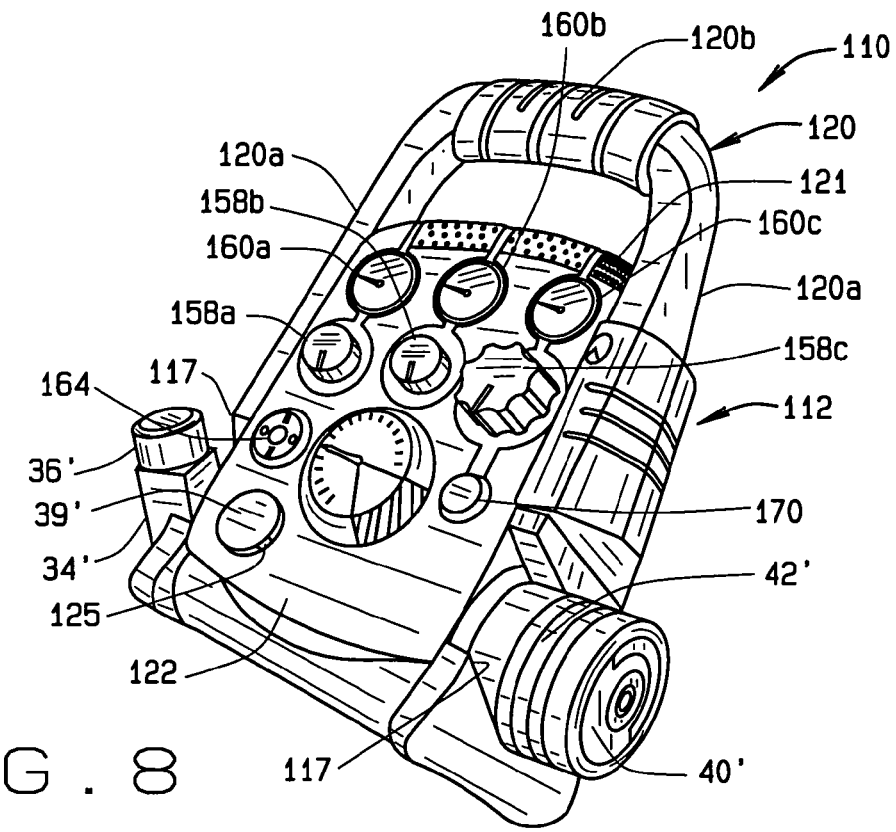
FIG. 8 is a front perspective view of the anesthetic machine of FIG. 7.
Figure 9:
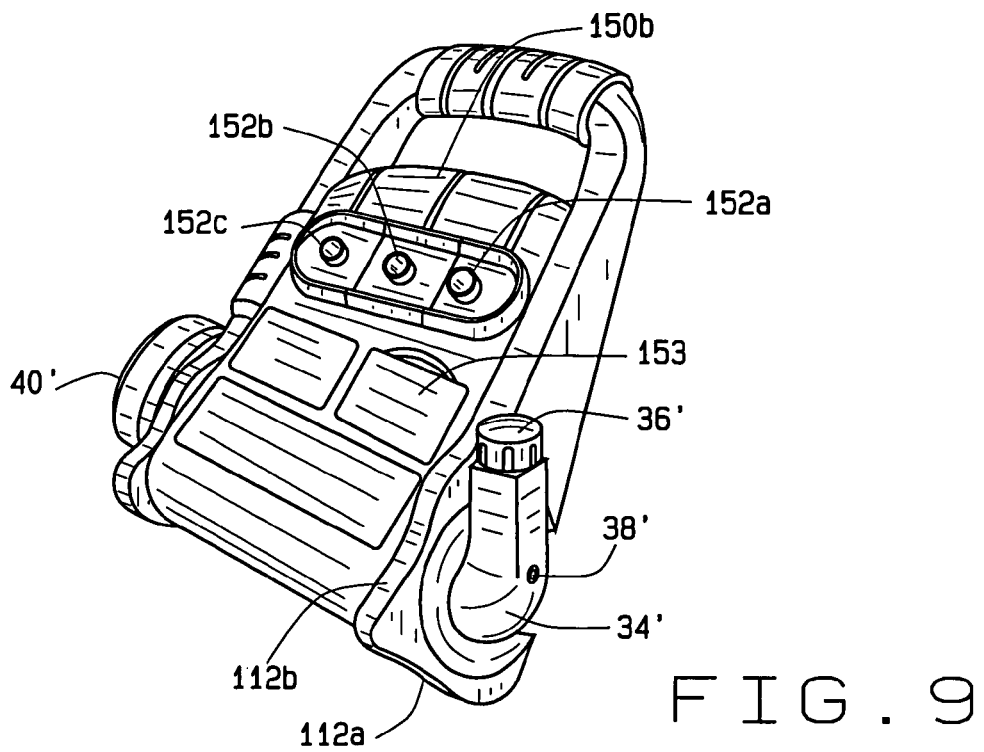
FIG. 9 is a rear perspective view of the anesthetic machine of FIG. 7.
Figure 9A:
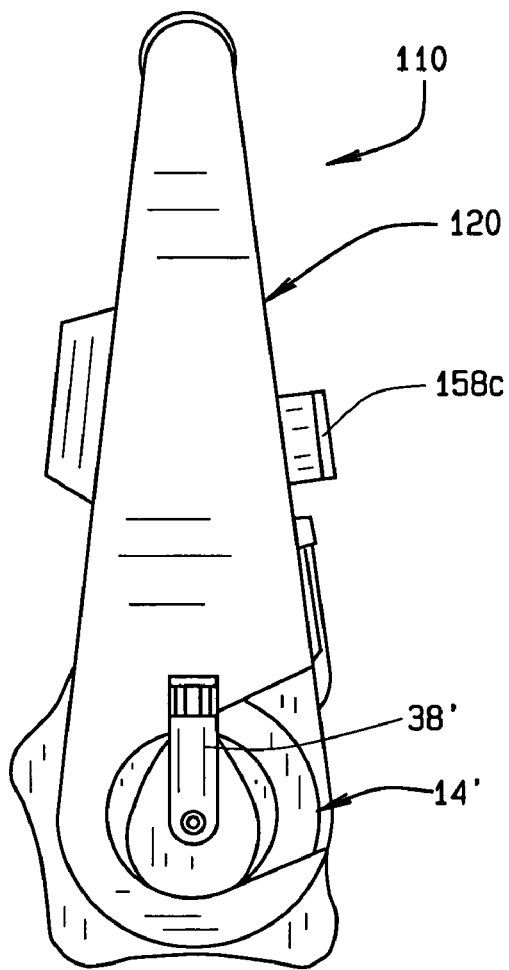
FIGS. 9A and 9B are right and left side elevational views of the anesthetic machine of FIG. 7.
Figure 9B:
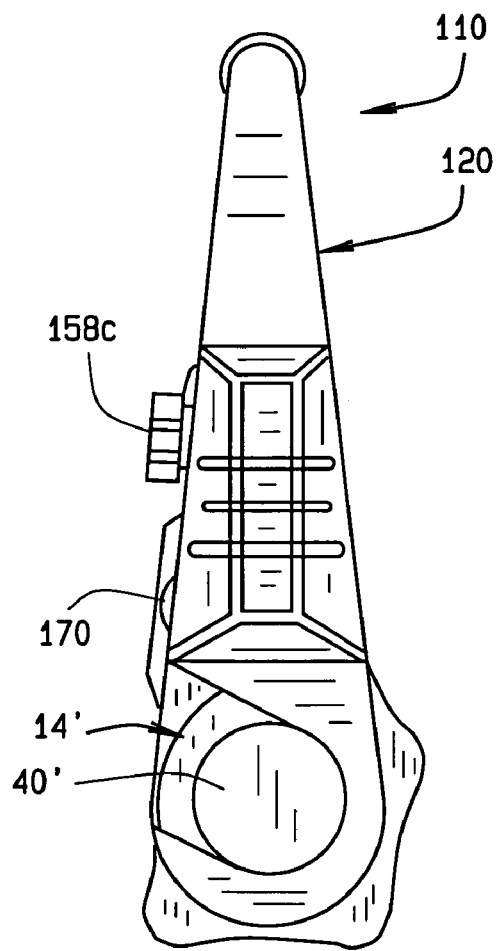

Turning to FIGS. 7-9, a second illustrative embodiment of the anesthesia machine is shown. The anesthesia machine 110 is similar in construction, and substantially identical in function to the anesthesia machine 10. Like the anesthesia machine 10, the machine 110 comprises a chassis 112 which removably receives the vaporizer 14'. The chassis 112 is concavely curved, as at 112a and 112b to define dual placement feet for the machine 110. The feet can be made from, or covered with, a non-slip rubber.

A cradle 116 is formed in the chassis to receive the vaporizer 14'. The cradle is defined by a channel corresponding generally to the size and shape of the vaporizer to receive the vaporizer. U-shaped cutouts 117 at the side of the cradle receive the control dial 40' and the fill chamber 34'. A carrier gas inlet 162 and carrier gas outlet (not shown), which correspond to the carrier gas inlet 62 and the carrier gas outlet 64 of the machine 10 are formed in the cradle 116 to receive the vaporizer outlet and inlet tubes 32' and 30', respectively. The anesthetic machine's carrier gas inlet 162 places the common gas outlet in fluid communication with the vaporizer outlet. Unlike the machine 10 where the gas flow paths are defined, in part, by removable tubing, the channels through which the gas flows are contained fully within the machine 110.

A panel 122 is received between the handle arms 120a. The handle arms 120a are sized such that there is a space between the handle gripping portion 120b and the top of the panel 122, to enable an operator to easily grasp the handle gripping portion to lift and carry the anesthetic machine 110.

The panel 122 is pivotally connected to the handle arms 120a substantially in the same manner to allow for pivoting of the panel 122 relative to the arms 120a, as seen in FIGS. 5A-D. As with the anesthetic machine 10, the machine 110 includes a lock which allows for the machine to be set in a desired orientation.

Unlike the machine 10, the panel 122 of the machine 110 has a forward portion 122a which can pivot away from a bottom portion along the top of the panel, as seen in FIG. 7. The panel forward portion 122a contains the gas dials 158a-c, the gas flow gauges 160a-c, the O$_2$ push button 170, the circuit pressure gauge, and the common gauge outlet port 164. Turning to FIG. 7, the panel front portion 122a includes an inwardly curved surface 123 near the free end of the panel section. The panel front portion 122a is sized so that it will extend over the vaporizer 14', and the surface 123 is positioned to overly the vaporizer and correspondingly shaped to the curvature of the vaporizer 14'. An opening 125 is formed in the panel section 122b, and is positioned such that the vaporizer gauge 39' will at least be visible through the opening 125. The panel section 122b includes any common mechanism to secure the panel section 122b in a closed position. Such mechanism can include clasps, posts which are grippingly or snappingly received in holes, etc. As can be appreciated, when the panel section 122b is in the closed position, as shown in FIGS. 8 and 9, the vaporizer 14' will be maintained in the machine 110. Because the vaporizer fill chamber and control dial are exposed, the vaporizer can be filled and set after the vaporizer has been placed in the machine 110. To remove the vaporizer 14' from the machine 110, the user need only lift open the panel top section 122b. The vaporizer 14' can then be simply lifted out of the cradle 116.

The machine's back surface 150b (FIG. 9) is substantially similar to the back surface 50b of the machine 10. The panel back surface includes ports or connectors 152a-c which receive the tubing from the sources of air, oxygen, and nitrogen oxide, respectively. The connectors 152a-c are spaced apart from each other, and the area around the connectors can be colored to correspond to the gas with which the particular connector is associated. In addition, a battery compartment 153 is provided in the back of the panel. The battery compartment 153 receives one or more batteries as may be necessary to power the electronic components of the machine 110, and the external devices which may be attached to the machine, as will be described below. The battery or batteries can be single use or rechargeable batteries. The use of batteries allows the machine 110 to be used where there is no available source of electrical power, or the power source is unreliable.

Illustrative views of a third embodiment of the anesthesia machine are shown in FIGS. 10-13. Like the anesthesia machine 10, the machine 210 comprises a chassis 112 which removably receives the vaporizer 14'. The chassis 212 is concavely curved, as at 212a and 212b to define dual placement feet for the machine 210. The feet can be made from, or covered with, a non-slip rubber.

Figure 12:
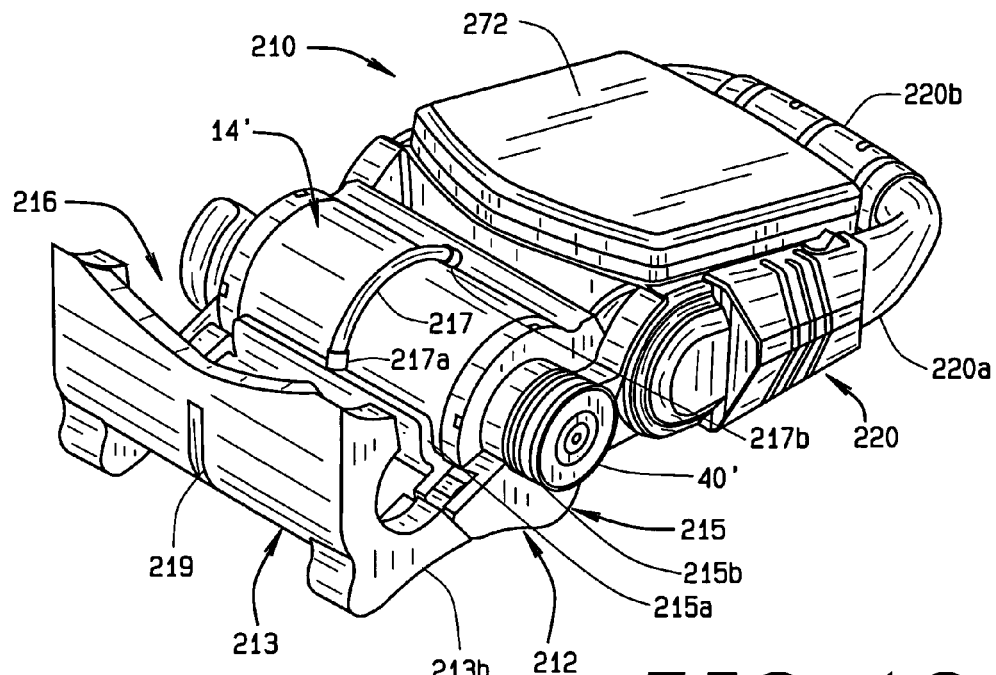
FIG. 12 is a perspective view of the anesthetic machine of FIG. 10 in a vaporizer receiving/removing position.

A cradle 216 is formed in the chassis to receive the vaporizer 14'. As seen in FIG. 12, the chassis 212 includes a forward section 213 and a back section 215. The chassis back section 215 includes a channel defined by a curved surface 215a which is shaped to receive the vaporizer 14'. As with the anesthesia machine 110, the chassis back section 215 includes ports which receive the inlet and outlet tubes 30' and 32' of the vaporizer 14'. The side walls of the chassis back section 215 have cutouts 215b forms therein. The cutouts 215b on the opposite side walls are sized and shaped to receive the vaporizer control dial 40' and the vaporizer fill chamber. Because one of the cutouts is formed to receive the control dial 40' and the other of the cutouts is formed to receive the fill chamber, the vaporizer can only be placed into the cradle 216 in one direction. Thus, a user will not inadvertently connect the vaporizer to the anesthetic machine improperly.

Figure 10:
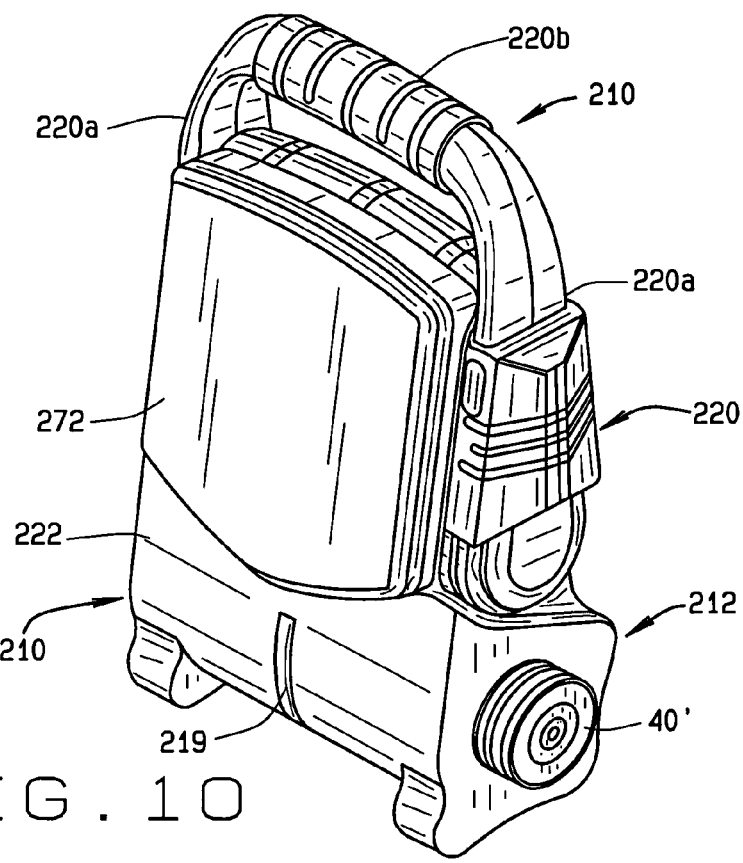
FIG. 10 is a front perspective view of a third illustrative embodiment of an anesthetic machine of the present invention; the machine being shown in a closed, carrying position.
Figure 11:
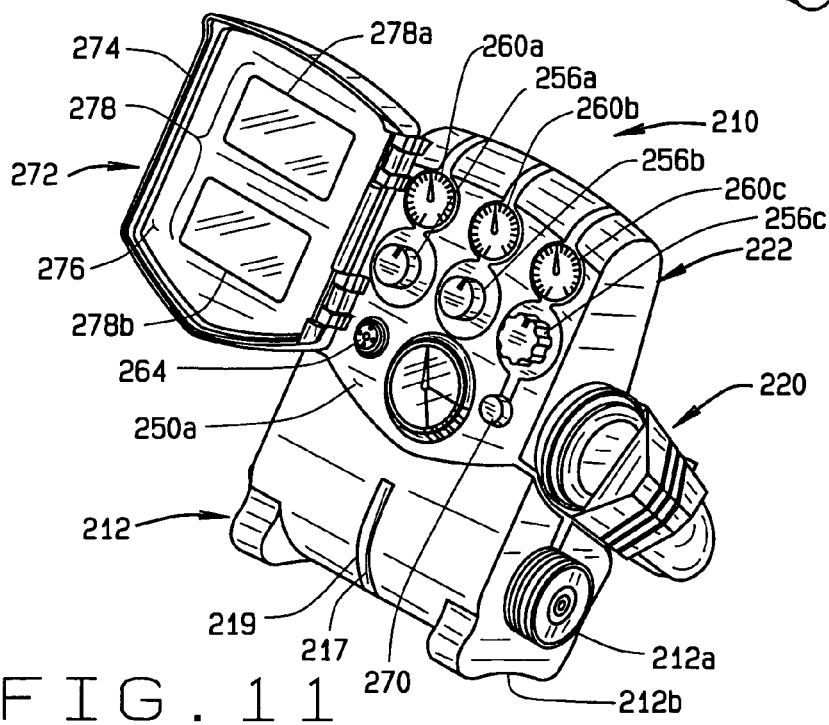
FIG. 11 is a front perspective view of the anesthetic machine of FIG. 10 in an open position for use.

The chassis front section 213 is hingedly connected to the back section 215 along the bottom of the chassis. Hence, the chassis can be moved between an open position, as shown in FIG. 12 in which a vaporizer 14' can be inserted into or removed from the chassis 216, and a closed position, as shown in FIGS. 10 and 11, in which the vaporizer 14' is secured in the chassis. The chassis front and back sections are provided with a locking element which will hold the chassis front section and back section together when the chassis is in the closed position. The side walls of the chassis front section include cutouts 213b which cooperate with the cutouts 215b of the back section 215 to encircle the end elements (i.e., the fill chamber and the control dial) of the vaporizer. Hence, when the vaporizer is received in the chassis, and the chassis is closed, all that is visible of the vaporizer is the control dial and the fill chamber.

The chassis is also provided with a transparent or translucent tube 217 which extends around the vaporizer body. As can be seen in FIG. 12, the tube 217, in combination with the chassis back section channel, defines a circle which surrounds the vaporizer. As seen, the tube 217 is received in connectors 217a,b on the opposite ends of the wall 215a that defines the chasses. The tube 217 can be disconnected from the connectors to allow for the vaporizer to be inserted into, or removed from, the chassis. Alternatively, the cradle and tube 217 can be sized such that the vaporizer can be slid axially under the tube 217 and into the cradle 216. The tube 217 is hollow, and is in fluid communication with the flow path of the anesthetic agent, as described briefly above, and as will be described in more detail below. The chassis front section 213 has a slot 219 through which the tube 217 can be seen, as best shown in FIG. 11. The tube 217 can be used by a practitioner to give a visual indication of the amount of anesthetic agent remaining in the vaporizer 14'.

Furthermore, the anesthesia machine can contain an anesthetic agent identification system, such as infrared spectroscopy, electrochemical sensors, ion mobility spectroscopy, color change chemistry, mass spectrometry, Raman spectroscopy, gas chromatography, density and molecular weight. Volatile anesthetics absorb infrared light. There are several absorption wavelengths that can be used; for example, a wavelength of about 10-13 mm is a common wavelength range. Light at this wavelength range is shone continuously, or by the push of a button on the machine. The light can be transmitted through the anesthetic vapor either in the anesthetic chamber of the vaporizer or through the tube 217. Light absorption is proportional to anesthetic vapor concentration. The Infrared device then transmits an output to a controller. The controller, using the infrared device output, determines the anesthetic agent contained in the vaporizer based upon the light absorption characteristics. This determination can then be displayed; for example, the agent name can be displayed on a monitor or the identifying color of the agent can be displayed either on a monitor or on the panel. Adsorption at other wavelengths may also be measured so that the agent being used can be identified automatically.

Anesthetics also have a characteristic density and molecular weight. Thus, the machine 210 also can be provided with a densitometry device for determining the density of the gas in the vaporizer or the density of the carrier gas. The densitometry output can be used to confirm the type of anesthetic contained within the vaporizer. Additionally, based upon the density of the gas, the amount of anesthetic agent in the gas can be determined, and hence, whether the amount of anesthetic agent entrained in the carrier gas is diminishing. The densitometry device will send a signal to the controller, which can then issue a warning to communicate the absence of anesthetic agent to the practitioner. The warning can be audible, and the machine 210 can include a speaker 121 (FIG. 8) to alert the physician to the fact that the amount of anesthetic agent is reaching a low level.

A panel 222 extends upwardly from the chassis 116. A handle 220 comprises a pair of arms 220a and a gripping portion 220 extending between the tops of the arms 220a. The handle arms 220a are sized such that there is a space between the handle gripping portion 220b and the top of the panel 222, to enable an operator to easily grasp the handle gripping portion to lift and carry the anesthetic machine 210. The handle arms 220a are pivotally connected to the panel 222, so that the handle can be moved between a carrying position (as seen in FIG. 10) and a support or stabilizing position (as seen in FIG. 11). In the stabilizing position, the handle 220 stabilizes the anesthetic machine so that the panel 222 is generally upright, and so that its controls can be easily seen and operated. As with the anesthetic machine 10, the arms 220a of the machine 210 include a lock which allows for the arms to be set in a desired orientation.

The panel front surface 250a is substantially similar to the panel front surface 150a of the machine 110. The panel front surface 256a includes gas control dials 260a-c and the associated gas pressure gauges 260a-c. The control dials 256a-c operate valves and are used to set the flow rate for the oxygen, nitrous oxide and air (which make up the carrier gas for the anesthetic agent). The gauges 260a-c show the pressure or flow rate for the separate gases. Additionally, the front panel includes a circuit pressure gauge, a gas outlet 264 (to which the patient tube is connected) and an oxygen flush activation button 270. The rear of the panel 222 is substantially identical to the rear of the panel 122 (FIG. 9) and will not be described herein.

Unlike the anesthesia machines 10 or 110, the machine 210 is provided with a display panel 272. The display panel 272 is pivotally connected to the panel 222 by means of hinges 273, and can be moved between a closed position (FIG. 10) and an open position (FIG. 11). The display panel 272 includes an outer rim 274 which surrounds and extends from a generally flat inner surface 276. The rim 274 is sized, such that when the display panel is closed, the panel inner surface 276 will be spaced at least slightly from the various control dials and gauges on the panel front surface 250a. In addition, the edge of the rim 274 is shaped to correspond to the shape of the panel front surface 250a.

Figure 13:
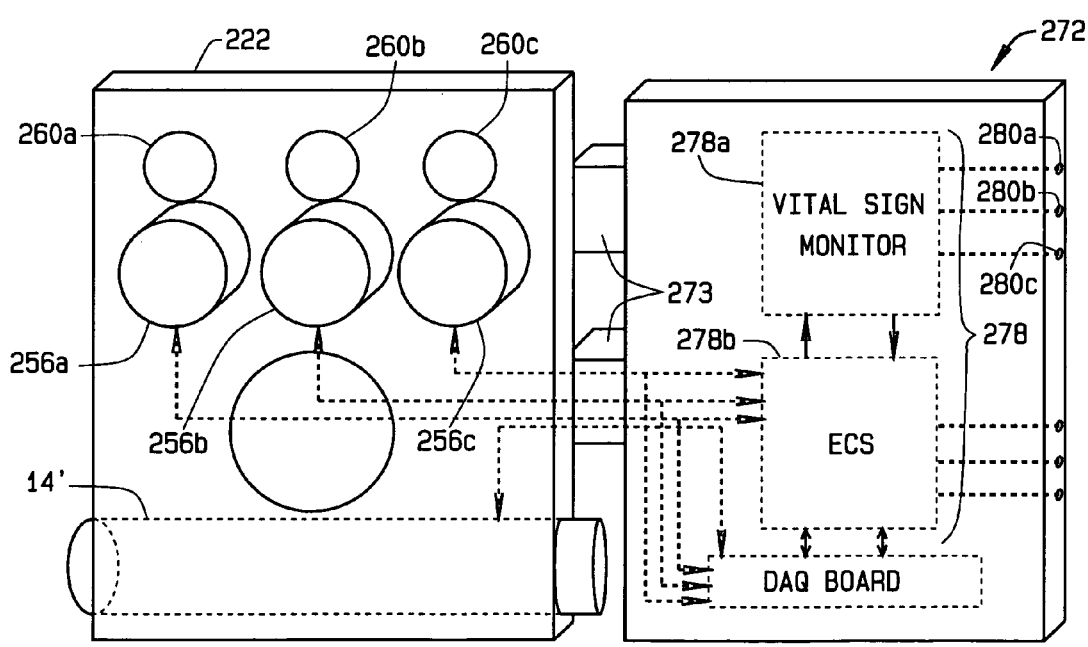
FIG. 13 is a schematic drawing of the anesthetic machine of FIG. 10, showing some of the components of the control system for the machine.

The display panel 272 includes a monitor 278. Although the monitor 278 is shown in FIGS. 11 and 13 to include two separate monitor or display portions 278a,b, the monitor can be a one-piece monitor. The display panel 272 also includes connector ports (three ports 280a-c are shown) which receive inputs from patient monitoring devices to monitor and display information relating, for example, to pulse, blood oxygen concentration, blood pressure, carbon dioxide concentration of exhaled breath, heart rate, ECG, etc. Although only three ports are shown, additional ports can be included, if desired. These ports receive the inputs from commercially available devices. The data (heat rate, pulse, etc.) is shown on the upper portion 278a. Additionally, the anesthetic machine can be provided with a data storage device (such as a memory card, for example), and the patient medical record can be read and stored on the memory card as well real time machine data.

As will be discussed below in more detail below, the anesthetic machine monitors the temperature, pressure and flow rate of the gas at various points in the machine. This data can also be displayed on the display monitor 278. Inasmuch as the patient data is displayed on the monitor upper portion 278a, the machine operating data is displayed on the monitor lower portion 278b. In addition, the display monitor can display notifications about the operation of the anesthesia machine. Such notices can include (1) the type of anesthetic agent, the amount of gas (i.e., oxygen, nitrous oxide, air) left in the respective tanks, amount of anesthesia agent remaining in the vaporizer, the percent of anesthetic agent in the carrier gas being delivered to the patient, and alerts regarding the operation of the system. Electrical connectors pass through, or are otherwise incorporated in, the hinges 273 to place the monitor 278 and the connector ports 280a-c in electrical communication with the controller, which is contained in the panel 222.

As can be appreciated from the above, the anesthetic machines 10, 110, and 210 are can be quickly and easily set up for use. The machines are relatively small. For example, the overall height of the machine can be about 15" to about 16" and the overall width can be about 5" to about 6". Further, the machine is relatively light, and can weigh under 100 pounds, and preferably under 60 pounds. Hence, the anesthetic delivery machine can be easily transported in a carrying device, such as a backpack, suitcase, etc. Further, the vaporizer can be surrounded by a sleeve of high durometer rubber to provide shock absorption to the vaporizer. This will reduce the effects of shock and vibration on the operation of the vaporizer. The sleeve will also thermally insulate the vaporizer to reduce heat loss or heat gain through the vaporizer wall.

Gas Flow and Control Of The Anesthesia Delivery Machine

Figure 14:
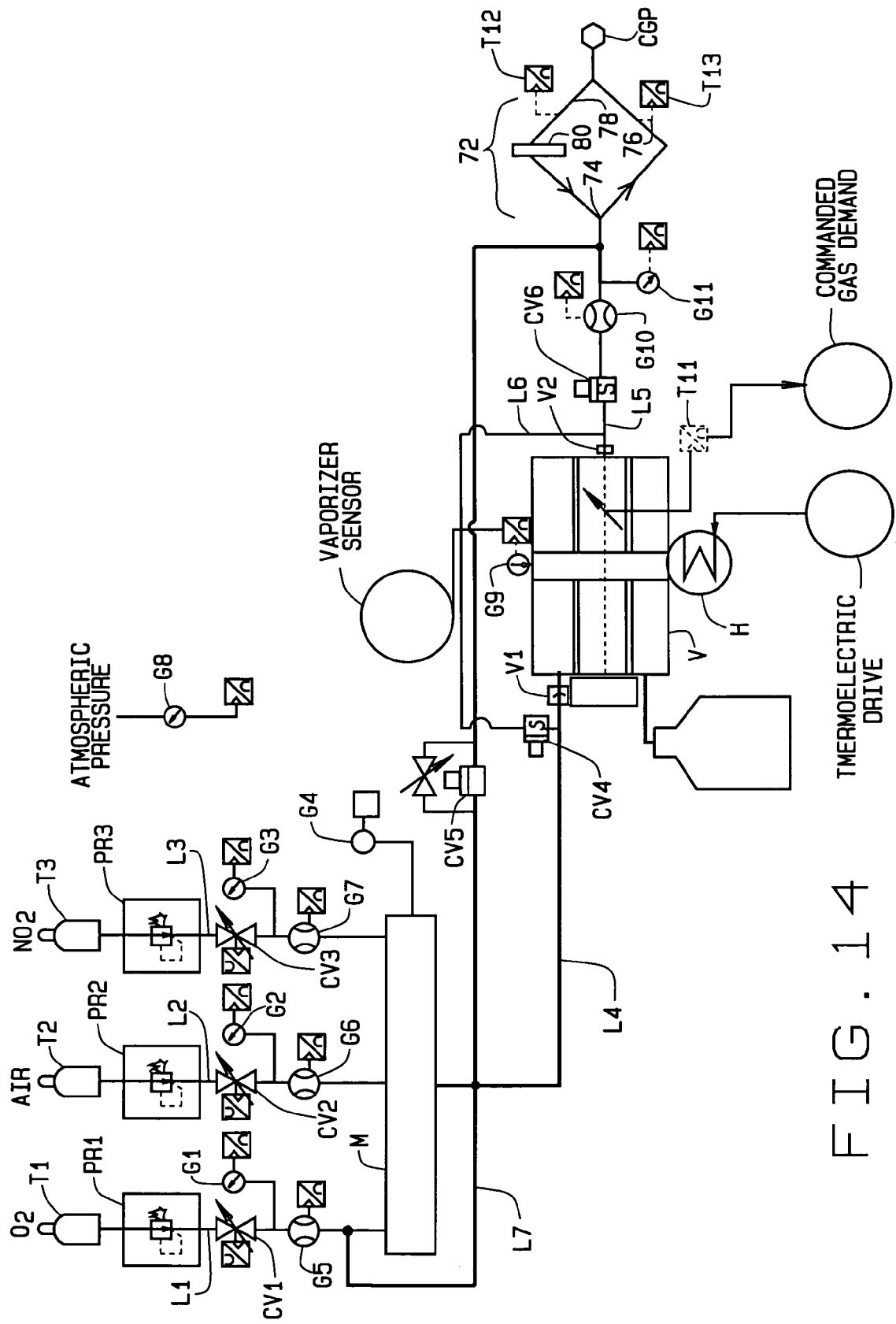
FIG. 14 is a block diagram of the gas flow and control system for the anesthetic machine.
Figure 14A:
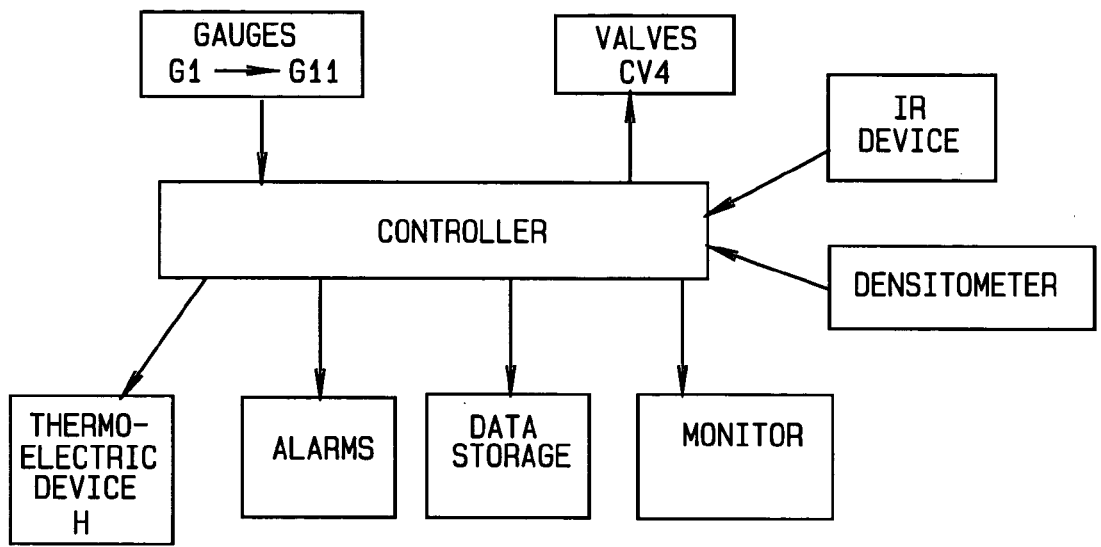
FIG. 14a is a block diagram of the controller for the machine.

Turning to FIG. 14, the gas flow path and control system for the anesthetic machine 10, 110, 210, 310 is shown in diagrammatic format. Initially, the gas flow path is as follows. Oxygen ($O_2$), air and nitrous oxide ($NO_2$) supplied, for example, by tanks T1-T3 or other sources of carrier gases as described above. Each tank is provided with a pressure regulating valve PR1-PR3. The tanks T1-T3 are connected to the anesthesia machine (i.e., device 10, 110, 210 or 310) by connecting lines L1-L3. These lines L1-L3 place the tanks T1-T3 in fluid communication with respective flow paths within the anesthesia delivery machine itself. Initially, the paths for the carrier gasses include manually adjustable control valves CV1-CV3. These control valves correspond, for example, to the controls 56a-c, 156a-c or 256a-c of the devices 10, 110 or 210, and are used to set the flow rate for the respective gas. Pressure gauges G1-G3 measure and display the pressure of the respective gas as the gas exits the control valves CV1-3. The gases then flow to a manifold M (contained within the panel 22, 122, 222) where the gases are combined to form a carrier gas. A gauge G4 measures and displays the pressure of the gas exiting the manifold. This pressure is displayed on the panel (22, 122, 222) as the circuit pressure gauge. The circular shape of the gauges shown in the drawings is illustrative only; the gauges can be any shape, and can be analog or digital gauges. The carrier gas exits the manifold along a line L4 and flows to the vaporizer V where the carrier gas picks up anesthetic agent. The carrier gas with the anesthetic agent entrained therein exit the vaporizer and is directed to the common gas port CGP along the line L5. One way valves V1 and V2 can be provided on opposite sides of the vaporizer to ensure the gas flows in the proper direction through the anesthetic machines. The valves V1 and V2 (which, for example, can be poppet valves) can be located in the vaporizer inlet and outlet or in the machine panel proximate the carrier gas inlet and carrier gas outlet.

In addition, a bypass line L6 splits off from line L4 to deliver carrier gas directly to line L5, thereby bypassing the vaporizer. A control valve CV4 in the line L4 or L6 controls the flow of carrier gas through the line L6. Valve CV4 effectively controls the ratio of carrier gas that by-passes the vaporizer to the amount of carrier gas that is directed to the vaporizer. For example, for a 20% ratio or split, 20% of the carrier gas would be directed through the by-pass line, and 80% of the carrier gas would be directed to the vaporizer to entrain anesthetic agent.

Figure 14D:
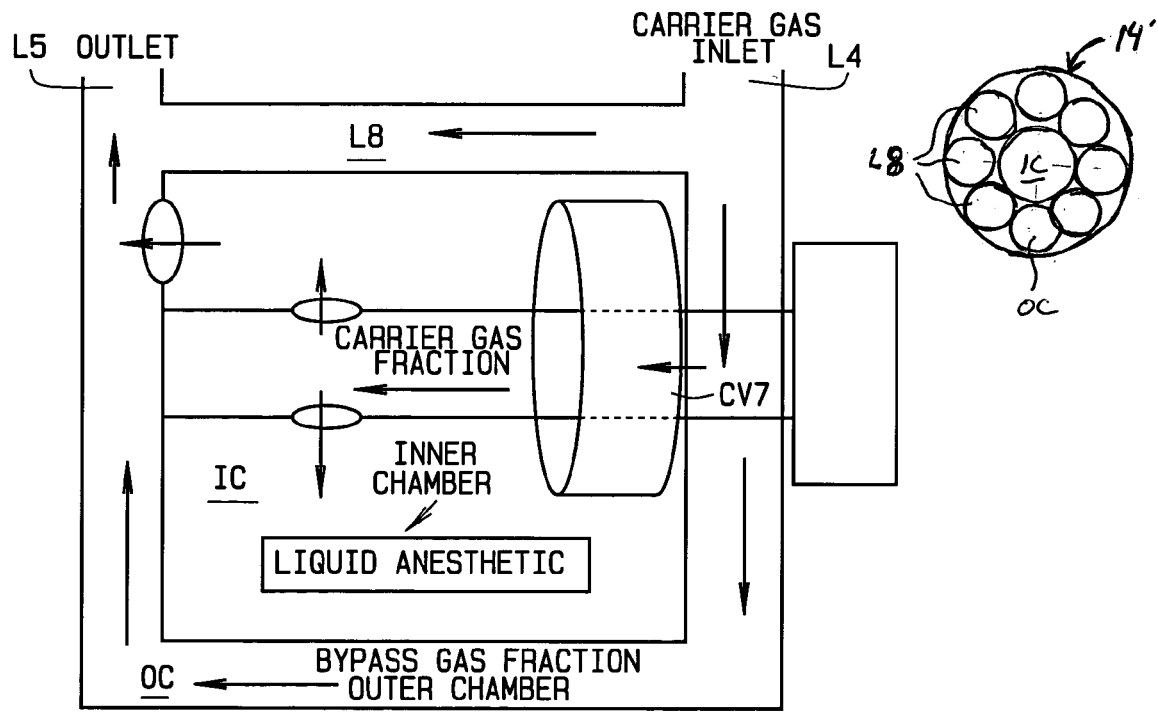
FIG. 14d comprises two diagrammatic drawings of the vaporizer.
Figure 14B:
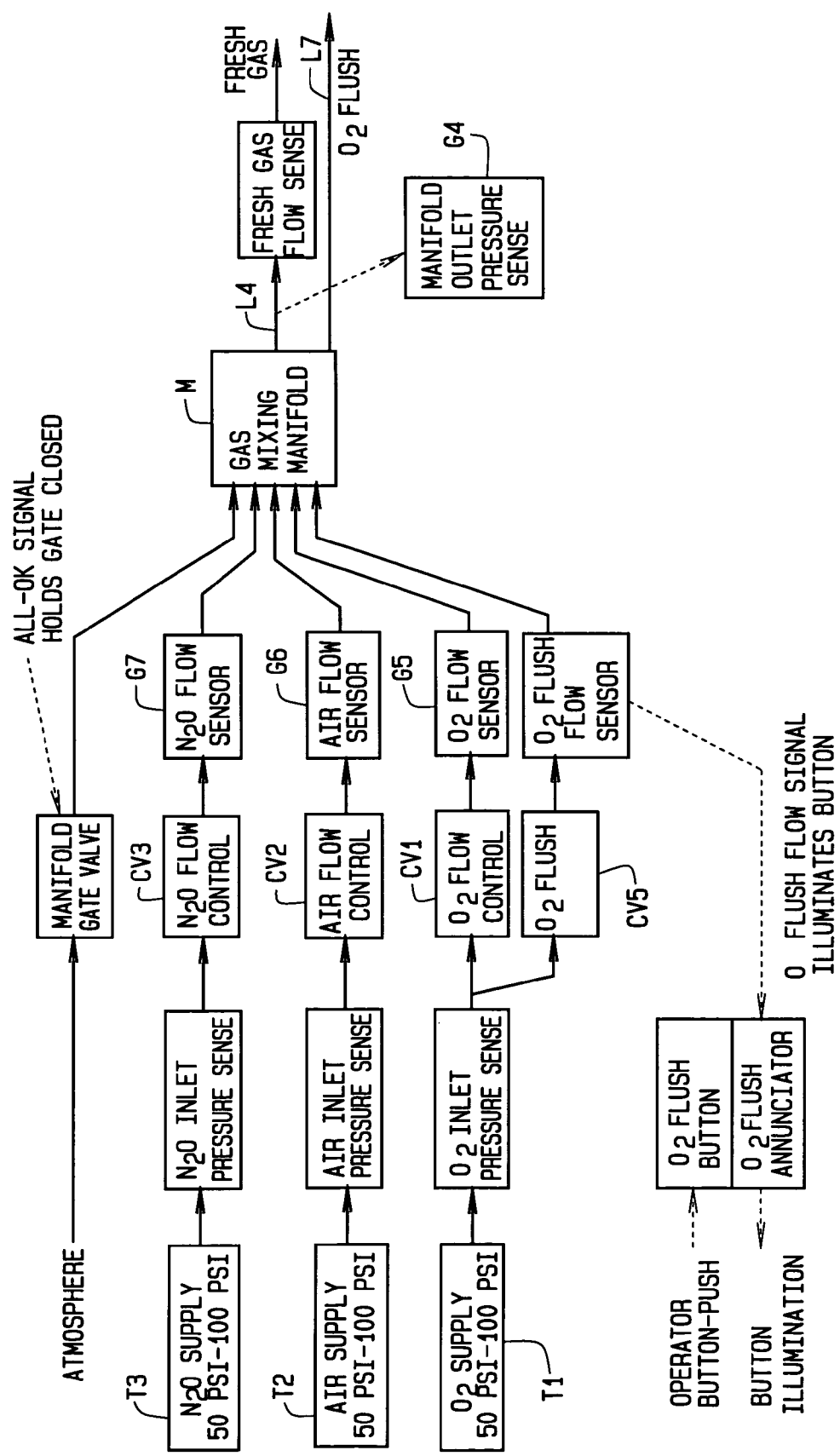
FIGS. 14b and c are two parts of a gas flow path diagram for the machine

The line L6 is an external by-pass. The vaporizer V in addition includes an internal by-pass L8. Turning to FIGS. 14c and 14d, the vaporizer can be seen to include an inner chamber IC and an outer chamber OC. The anesthetic agent is contained within the internal chamber and is entrained by the carrier gas which enters the internal chamber. As seen in FIG. 14d, the outer chamber OC can, for example, comprise a plurality of lumens or flow passages which surround the inner chamber. A valve CV7 is positioned at the entrance to the inner chamber. The valve CV7 is controllable, and thus, the fraction of the carrier gas entering the vaporizer V and which then enters the inner chamber IC can also be controlled.

The ability to control the amount of carrier gas which (1) enters the vaporizer and (2) enters the vaporizer inner chamber to entrain anesthetic agent, allows for a higher degree of control of the air flow through the vaporizer than has heretofore been allowed. In addition, the ability to control the degree to which the valve CV7 is opened also allows for the device to be switched between a plenum and draw over mode.

By partially closing the valve CV7, the inspiratory resistance can be increased, and by opening the valve CV7, the inspiratory resistance can be decreased. Thus, by opening the valve CV7, the device can be switched to a draw over mode in which the delivery of gas to the patient is dependant upon the patient's inhalation. This can also be accomplished by changing the diameter of the entrance to the tubes which make up the outer chamber. In this instance, the outer chamber tubes would be provided with controllably valves in addition to or in lieu of the valve CV7 at the entrance to the vaporizer inner chamber.

An oxygen push line L7 connects the oxygen path (from just after the oxygen control valve CV1 to the line L5 just prior to the common gas port CGP. A control valve CV5 can be operated to open the line L7 to deliver oxygen directly to the common gas port. As seen in the diagram of FIG. 14, the oxygen push or oxygen flush line L7 bypasses the manifold and the vaporizer, so that, when necessary, a bolus of oxygen can be delivered directly to the patient. As can be appreciated, the valve CV5 is a normally closed valve, and is opened only upon activation of the valve. When the valve CV5 is deactivated, the valve will return to its closed position.

In addition to the gauges noted above, the anesthesia machine is provided with flow gauges G5-G7 which measure the flow rate of the three gases prior to entry of the gases into the manifold M. A gauge G8 measures atmospheric pressure; a gauge G9 measures the temperature within the vaporizer; gauges G10 and G11 measure the flow rate and pressure, respectively, of gas exiting the vaporizer. Each gauge is provided with an associated transducer. In addition, the anesthesia delivery machine is provided with a sensor and associated transducer T11 which measures the pressure within the vaporizer. In addition, if the device is provided with a breathing circuit 72, the device will be provided with sensors and associated transducers T12 and T13 in lines 78 and 76, respectively, which measure the end-tidal $CO_2$ concentration in the exhalation branch and the $O_2$ concentration in the inhalation branch of the breathing circuit, respectively. Lastly, the device can be provided with a control valve CV6 and associated transducer in the line L5 to control the flow rate of gas exiting the vaporizer.

The transducers are all in communication with the controller and send the controller signals indicative of the information supplied by the various gauges. For example, the transducer for the gauge G5 will send the controller a signal indicative of the flow rate of oxygen entering the manifold M. The values of any or all of the gauges can be displayed on the display screen 278.

At least the valves CV4 and CV7 are controllable valves. That is, the degree to which the valves are opened can be controlled by the controller. The valves CV4 and CV7 can, for example, be solenoid operated valves. The valves CV1-CV3 are shown to be manually operated valve (being operated by control knobs on the anesthesia machine panel). However, these too could be controllable valves, which would then allow for digital controls for the valve settings.

The controller uses the outputs from the various gauges and transducers to control the valves CV4 and CV7 to adjust the degree to which the valves are opened in order to adjust the flow rate of carrier gas to inner chamber IC of the vaporizer V to maintain the desired concentration of the anesthetic agent in the gas stream delivered to the patient substantially constant. By adjusting the valves CV4 and CV7, the flow rate of the carrier gas into the vaporizer inner chamber IC will be increased or decreased. As the flow rate increases, the amount of anesthetic agent entrained by the carrier gas will increase;

conversely, as the flow rate of the carrier gas decreases, the amount of anesthetic agent entrained by the carrier gas will decrease. Hence, by using the controller to control the valves CV4 and CV7, the operator can set the desired relative percentages of the three gases using the valves CV1-CV3 and set the desired anesthetic concentration using the dial 40, 140 or 240, and will not have to adjust the flow of the three gases to adjust the anesthetic agent concentration. Rather, the anesthetic agent concentration in the outlet stream is controlled by adjusting the flow rate of the carrier gas into the vaporizer at the valve CV4.

Although the flow rate of carrier gas to the vaporizer inner chamber is described to be controlled by two valves and two by-pass lines, the carrier gas flow can be adequately controlled using a single by-pass. Thus, one of the by-pass lines and the valve associated with the by-pass line could be omitted.

Because the vapor pressure of the anesthetic agent and the carrier gases are dependent upon temperature, and because vaporization of the anesthetic agent will cause cooling within the vaporizer, the device is provided with a thermoelectric device H. The thermoelectric device can be a thermoelectric heat pump, such as a Peltier junction, which can function to either cool or heat the vaporizer. As noted above, the anesthesia machine is provided with a temperature gauge G9 which monitors the temperature within the chamber. The partial pressures for anesthetic agents are typically determined at STP (standard temperature and pressure), or about 25° C. and 1 atm. Hence, the controller controls the thermoelectric device H to maintain the vaporizer chamber at about 25° C. To place the vaporizer pressure gauge G9 and temperature sensor T11 and the heater H in communication with the controller, the vaporizer V and the anesthetic machine chassis are provided with connections, in manners that are well known in the art. The temperature in the vaporizer can be controlled in accordance with the following formula:

$$TE_{drive}=[T_c-T_v]*[f(K_1 P_{atmos}+k_2 P_v)],$$

where, $TE_{drive}$ is the change in temperature (or $\Delta T$) needed to bring the vaporizer chamber back to the desired or control temperature;

$T_c$ is the control or set temperature;

$T_v$ is the vaporizer chamber temperature as measured by the temperature gauge G9;

$P_{atmos}$ is the ambient atmospheric pressure as measured by the pressure gauge G8; and $P_v$ is the pressure within the vaporizer chamber as measured by the sensor and associated transducer T11.

In addition to controlling the by-pass valve CV4, actuators can be associated with the one-way valves V1 and V2 at the vaporizer inlet and outlet (or the carrier gas outlet and carrier gas inlet of the panel). These actuators can be in communication with the controller to control the aperture of the one-way valves, in order to increase or decrease the carrier gas flow rate, in order to achieve a desired gaseous mixture and anesthetic concentration The heart and soul of an anesthesia machine is the anesthetic vaporizer. The principles that govern the operation of a vaporizer, which are rooted in physical science, are vapor pressure, boiling point, gas concentration, heat of vaporization, specific heat and thermal conductivity. Any anesthetic vaporizer design must consider these principles. Vaporizer performance and thus quality of an anesthesia machine are affected by how well the vaporizer is designed to insulate it from the effects of temperature, pressure and carrier gas flow rates.

Theory of Variable Bypass Vaporizers

The vapor pressure in a vaporizer that operates on variable by-pass principle, which receives fresh gas flow from a manifold as illustrated in FIG. 15, can be determined as follows:

Let the fresh gas flow from the manifold be designed, $F_g$, and carrier gas fraction into the vaporizer be $F_c$, while the by-pass fraction is $F_b$ (FIG. 1). Let $F_a$ be the fraction of anesthetic gas within the vaporizer.

Given, the fraction of anesthetic gas and carrier gas, the vapor pressure of anesthetic ($V_a$) can be determined as follows:

$$V_a = \left(\frac{F_a}{F_a+F_c}\right) \cdot 760 \text{ mmHg} \quad \text{(Eq. 1)}$$

The vapor pressure can also be expressed using units other than mmHg, such as psi (pounds per square in), cmH$_2$O (centimeters of water). In the case of psi, the atmospheric pressure is 14.7 psi.

It follows that the vapor pressure of the anesthetic agent is affected by the volume of carrier gas, $F_c$ admitted into the vaporizer.

When $F_c$ is zero, the vapor pressure of anesthetic, $$V_a = \frac{F_a}{F_a} \cdot 760 = 760 \text{ mmHg} \quad \text{(Eq. 2)}$$

Total Gas Flow Rate

From the preceding relationships, the total gas flow rate, $$F_T = F_a + F_c + F_b \quad \text{(Eq. 3)}$$

Calculation of Anesthetic Gas Flow Rate

Assuming that we know the vapor pressure of the anesthetic ($V_a$), fresh gas ($F_g$), bypass gas ($F_b$), and carrier gas ($F_c$) flow rates, we can find the anesthetic gas flow rate ($F_a$).

Consider the anesthetic agent Halothane, which at 20° C. has a vapor pressure ($V_a$) equal to 243 mmHg. Suppose, $F_g$=7 liters, $F_b$=5.5 liters, $F_c$=1.5 liters, from Eq. 1, $$\left(\frac{F_a}{F_a+F_c}\right) = \frac{V_a}{760} = 243/760 \text{ mmHg} \quad \text{(Eq. 4)}$$

Based on this relationship we can find the relationship of anesthetic gas fraction (or concentration) of Halothane to various flow rates of carrier gas, $F_c$.

Solving Eq. 4 in terms of $F_a$, we have, $$760 F_a = 243(F_a + F_c) \quad \text{(Eq. 5)}$$

$$760 F_a = 243 F_a + 243 F_c \quad \text{(Eq. 6)}$$

$$760 F_a - 243 F_a = 243 F_c \quad \text{(Eq. 7)}$$

$$517 F_a = 243 F_c \quad \text{(Eq. 8)}$$

Thus the ratio of anesthetic gas fraction to carrier gas flow rate in this example, $F_a=(243/517)F_c=0.47F_c$. If carrier gas flow is zero, anesthetic gas fraction will be zero.

It follows for Halothane, that the anesthetic gas fraction is related to carrier gas flow rate by the relationship, $$F_a=(243/517) \cdot F_c \quad \text{(Eq. 9)}$$

When $F_c$=1.5 liters for example, we have $$F_a=243(1.5)/517=364.5/517 \text{ liters}=0.71 \text{ liters}.$$

Similar relationships can be determined for other anesthetic agents, such as Ethrane, Isoflurane and Sevoflurane can be derived, using their vapor pressures, and the flow rates given.

Establishing $F_c$ Value to Achieve a Desired $F_a$

To achieve a specific fraction of anesthetic gas, we would specify the fraction of anesthetic ($F_a$) and solve for $F_c$.

To generate an anesthetic gas fraction of Sevoflurane equal to 0.71 liters, we would find the necessary carrier gas flow, $F_c$ using Eq. 9, as follows:

$$F_a=(243/517) \cdot F_c,$$

$$\text{So } F_c=F_a(603/157); F_c=0.71(603/157)=2.73 \text{ liters approx.}$$

Using Eq. 9, we can generate a plot of required carrier gas flow rates for various fraction of anesthetic gas. The determined straight line relationship between $F_a$ and $F_c$ (Eq. 9) can be used by the controller to control the valve CV4. Because vapor pressure varies with temperature, the controller maintains the vaporizer chamber temperature at temperature of about 20-25° C. so that the relationship of Equation 9 can be relied upon to control the valve CV4.

Derivation of Total Gas Flow Rate ($F_T$)

The total gas flow rate is equal to the fraction of anesthetic gas, $F_a$, plus fraction of carrier gas, $F_c$, plus fraction of by-pass gas, $F_b$, which is given as follows:

$$F_T=F_a+F_b+F_c \quad \text{(Eq. 10)}$$

Based on the preceding flow rates given, the total flow would be $$F_T=710+5,500+1,500=7,710 \text{ milliliters}.$$

Percent Concentration of Anesthetic

The percentage of anesthetic gas fraction within the vaporizer that is delivered, is equal to the percent concentration of the anesthetic in the total flow, and can be calculated as a fraction of the total gas flow as follows:

$$\%\text{Concentration}=(F_a/F_T) \cdot 100\% \quad \text{(Eq. 11)}$$

Based on the preceding calculation, $F_a$=710 milliliters, and $F_T$=7,710 milliliters, therefore $$\%\text{Concentration}=(710/7710) \cdot 100\%=9.21\%$$

This means that the concentration of Halothane in the total gas flow is 9.21%.

Effect of Temperature on Anesthetic Gas Concentration

All anesthetic agents are volatile, and require varying degrees of thermal excitation to be transformed from liquid to vapor; which is determined by the specific heat of the anesthetic. When the temperature of the anesthetic inside a container closed to the atmosphere is raised, molecules of the liquid will break away from the surface and enter the surface above it, forming a vapor. These molecules bombard the walls, creating a pressure called the vapor pressure. If the container is kept at constant temperature, eventually equilibrium is formed between the liquid and vapor phases so that the number of molecules in the vapor phase remains constant. If after equilibrium, heat is supplied to the container, the equilibrium will be shifted so that more molecules will enter the vapor phase, creating a higher vapor pressure. On the other hand if heat is taken away, molecules will return to the liquid phase and the vapor pressure will be lower. This ability to increase or lower the vapor pressure affects the concentration of the anesthetic vapor and the accuracy of the vaporizer output regardless of the dial setting. Thus, vapor pressure depends only on the liquid and the temperature, and not on the barometric pressure within the range of pressures encountered in anesthesia.

Vaporizer output is only linear in the range of 25-30° C., which is room temperature. Energy is required for the molecules of a liquid to change into vapor. This is supplied by the liquid itself. Regardless of the vaporizer setting, without thermal compensation, the vaporizer cools as the liquid anesthetic vaporizes, and results in a decrease in concentration, or volume percent delivered to the patient. This heat of vaporization is supplied in part by the remaining anesthetic, causing further drop in temperature and decrease in vaporizer output. Vaporizer output does not terminate instantaneously, but declines with time. This phenomenon is illustrated with the graphs of FIG. 16 which show the drop in temperature of a traditional vaporizer chamber over time. This drop in temperature in a traditional vaporizer chamber is due to evaporative cooling, caused by the evaporation of the anesthetic agent, as just noted.

The heat of vaporization is the number of calories needed to convert a gram (1 g) of a liquid into vapor; or the number of calories required to convert a cubic centimeters (1 cc) of liquid into vapor. The heat of vaporization per gram (Hv/g) can be converted to heat of vaporization per cubic centimeter (Hv/cc) by multiplying the former by the density of the liquid.

Regardless of how well a vaporizer is calibrated and controlled, it is important to note that the maximum vaporizer output is determined by the vapor pressure of the anesthetic agent. This is equal to the minimum alveolar concentration (MAC) of the anesthetic. Thus, the vapor pressure of the anesthetic determines the maximum concentration a vaporizer can deliver at the highest dial setting.

Because of this fact appropriate patient sedation requires that the vaporization deliver the concentration dialed by the physician, during induction and maintenance. When this is not the case the patient will not be adequately anesthetized.

Since the vapor pressure of an anesthetic changes with temperature, the dialed concentration will not be equal to the delivered concentration; That is, the amount of anesthetic agent entrained will decrease over time as illustrated above. To counter this phenomenon and to assure accuracy of anesthetic delivery the temperature compensation means is necessary. The temperature compensation operates as discussed above. With the temperature of the vaporizer chamber maintained at the set temperature (i.e., at between 25-30° C.), the pressure in the chamber will remain substantially constant, the partial pressure of the anesthetic agent will remain substantially constant, and hence, the percent of anesthetic agent entrained will remain substantially constant.

Effect of Barometric Pressure

Existing vaporizers are calibrated at STP (standard temperature and pressure). At sea level, pressure is 760 mmHg. The effect of changes in temperature on vapor pressure when the temperature changes from 20° C. to a new value was discussed above.

Because the vapor pressures of anesthetic are determined at 760 mmHg, it must be noted that the boiling point of a liquid will change when the environmental pressure changes. As a result it is important to take this into account when operating an anesthesia machine in places above or below sea level.

When the atmospheric pressure changes the percent concentration delivered by a vaporizer must be adjusted.

Equation 11 gave a method for finding percent concentration of anesthetic delivered by a vaporizer.

Equation 11 can also be expressed as a function of the vaporizer flow, vapor pressure and barometric pressure, as follows:

$$\% \ Conc = F_a \cdot \frac{P_V}{P_B - P_A} \qquad \text{(Eq. 13)}$$

In this mathematical relationship, $F_a$ is the vaporizer dial setting (or diluent flow), $P_v$ is the vapor pressure of the anesthetic at ambient temperature, and $P_B$ is the barometric pressure. Alternatively, this can be expressed in terms of diluent flow of anesthetic vapor fraction ($V_D = F_a$), fresh gas flow to the vaporizer ($V_F = F_c$), vapor pressure ($P_v$), and atmospheric pressure ($P_A$). In this case, $$\% \ Conc = \frac{V_F \cdot P_V}{P_A(V_F + V_D) - (P_V \cdot V_D)} \cdot 100 \qquad \text{(Eq. 14)}$$

Effect of Anesthesia Circuit on Vaporizer Performance

It is important to note therefore, based on the preceding mathematical relationships that the actual concentration may differ from the dialed concentration, depending on how the vaporizer is used. When the vaporizer is used as an out-of-system vaporizer, vaporizer output (measured at the outlet) should be equal to vaporizer concentration. When it is used as an in-circle vaporizer, because the vaporizer receives, in addition to the fresh gas flow, gas containing anesthetic not taken up by the patient, the vaporizer concentration and vaporizer output may not be equal. By automatically comparing the concentration of anesthetic in the common gas outlet against desired concentration, carrier gas flow can be regulated to achieve desired concentration. This is accomplished by controlling the variable aperture valve CV4 that is located before the vaporizer inlet, and which has a one-way communication path with the carrier gas flow source, to reduce or increase flow rate.

In existing anesthesia machines, low pressure fresh gas flow to the vaporizer is regulated by control knobs on a manifold. The knobs on the manifold are additive, thus a high flow setting of 3 lpm and a low flow setting of 0.4 lpm yields a total output at the common gas supply of 3.4 lpm. As has been shown, the carrier gas fraction ($F_c$) that enters the vaporizer affects the fraction of anesthetic vapor ($F_a$).

In a closed anesthesia circuit, where the patient's exhaled gas is scrubbed of $CO_2$ and return to the patient via the inspiratory limb of the breathing circuit, the anesthetic concentration delivered will not be the same as that set on the vaporizer. It will include the scavenged anesthetic.

The change in concentration of a volatile anesthetic that is carried in a fresh gas with time can be expressed as a first order kinetic equation, as follows:

$$F_i = F_{set} e^{(1-t/k)} \qquad \text{Eq. 15}$$

where, $F_i$=concentration inspired (in circuit), $F_{set}$=concentration desired (set on vaporizer), k=time constant, and t=time.

The time constant is obtained by dividing the volume of the circuit in liters by the amount of fresh gas flow in liters per minute. A circle system for example with a volume of five liters and fresh gas flow of five liters per minute has a time constant equal to one minute. If the gas flow is changed to one liter per minute, the time constant is changed significantly to five minutes. Note that the volume of the circle system includes not only the tubing but also the volume of the absorber canister.

When the clinical situation requires rapid changes in anesthetic depth, the time delay in attaining anesthetic depth with low flow is historically overcome by the physician by increasing the carrier gas flow rates until the desired anesthetic depth has occurred. Once the depth of anesthesia has been achieved, it can be maintained by resuming low fresh gas flows. Instead of the manual approach employed in the past, the physician can instruct the closed-loop controller of the present machine to increase the gas flow rate by entering the desired flow rates on a key pad, which triggers a signal to the variable aperture valve CV4 to increase or decrease flow rate. The physician can verify that the desired concentration of anesthesia has been reached by simultaneously comparing the concentration at the "Y" of the breathing circuit leading to the patients breathing mask; measuring end-tidal $CO_2$ in the exhalation branch of the circuit, and $O_2$ concentration in the inhalation branch of the circuit.

It follows that a well designed vaporizer must compensate for the limiting effects of temperature, pressure, and carrier gas flow rate, and inspiratory resistance, which is a function of the vaporizer pluming as well as the length and diameter of the circuit.

As various changes could be made in the above constructions without departing from the scope of the invention, it is intended that all matter contained in the above description or shown in the accompanying drawings shall be interpreted as illustrative and not in a limiting sense. For example, although not shown in the drawings, the anesthetic machines could be provided with cables or other power supplies which can be plugged into a wall outlet in situations in which an area's electrical power supply is available and dependable. The display panel 272 of the anesthetic machine 210 (FIG. 11) could be omitted if desired. These examples are merely illustrative.

The invention claimed is:

1. A portable anesthetic delivery device comprising:
   a chassis comprising a cradle which removably receives a vaporizer; said vaporizer comprising a vaporizer input and a vaporizer outlet;
   a panel extending up from said chassis; said panel comprising a gas flow path, said gas flow path having gas inputs which receive carrier gases from sources of carrier gases, a manifold which combines the gases; a carrier gas outlet and a carrier gas inlet connectable to the vaporizer input and vaporizer outlet, respectively, a common gas port to which a patient cannula can be connected, and flow control devices in the gas flow path to control the flow rate of the carrier gases into the device;
   a support comprising a pair of arms and a member extending between an end of said arms;
   at least one of said panel and said support being pivotal relative to other of said panel and support; whereby, said device is selectively movable between a carrying position in which said support and said panel lie generally in a common plane and a use position in which said panel is angled relative to said support, such that said support in conjunction with said chassis maintain said panel in a generally upright position to facilitate use of the device.

2. The portable anesthetic delivery device of claim 1 including a lock mechanism to maintain the support in a desired position.

3. The portable anesthetic delivery device of claim 1 including external tubing which places said carrier gas outlet in communication with said vaporizer inlet and which places said carrier gas inlet in communication with said vaporizer outlet.

4. The portable anesthetic delivery device of claim 1 wherein said vaporizer inlet and outlet comprise tubes extending from a side surface of said vaporizer; said carrier gas outlet and said carrier gas inlet comprising ports in said cradle which receive said vaporizer inlet and outlet tubes.

5. The portable anesthetic delivery device of claim 1 comprising a vaporizer lock member which holds said vaporizer in said chassis.

6. The portable anesthetic delivery device of claim 5 wherein said vaporizer lock member comprises said panel; sand panel including a forward portion and a rear portion; said forward portion being sized to extend over said vaporizer; said forward portion being hingedly connected to said rear portion to be movable from an open position in which said vaporizer can be inserted into or removed from said cradle and a closed position in which said vaporizer is held in said cradle.

7. The portable anesthetic delivery device of claim 6 wherein said panel front portion is hingedly connected to said panel rear portion along a top of said panel portions.

8. The portable anesthetic delivery device of claim 5 wherein said chassis comprises a forward portion and a back portion; one of said chassis forward and back portions being movable relative to the other of said chassis portions; said chassis portions being movable between an open position in which said vaporizer can be removed from or inserted into said chassis and a closed position in which said vaporizer is secured in said chassis.

9. The portable anesthetic delivery device of claim 8 wherein said chassis comprises a pair of spaced apart clasps; said clasps each comprising a fixed member and a movable member; said movable member being pivotally connected to said fixed member; said clasp members having a surface conforming to the shape of the vaporizer and including a connector to maintain said clasp members in the closed position.

10. The portable anesthetic delivery device of claim 9 wherein said clasp member connector comprises a latch.

11. The portable anesthetic delivery device of claim 1 wherein said flow path comprises a tube which at least partially extends around said vaporizer; said tube being at least in part transparent or translucent; said transparent or translucent portion of said tube being visible; said tube providing a visual indication of the amount of anesthetic agent remaining in said vaporizer.

12. The portable anesthetic delivery device of claim 1 including an anesthetic agent detector; said anesthetic agent detector comprises a light transmitter operable to pass light of a predetermined wavelength through anesthetic vapor and a light receiver which receives the light passed through the anesthetic vapor; said receiver producing a signal indicative of the light absorbed by the anesthetic agent.

13. The portable anesthetic delivery device of claim 12 wherein said light transmitter and light receiver of said anesthetic agent detector are located in said anesthetic receiving chamber of said vaporizer.

14. The portable anesthetic delivery device of claim 12 wherein said flow path comprises a tube which at least partially extends around said vaporizer; said tube being at least in part transparent or translucent; said light transmitter and light receiver of said anesthetic agent detector being located on opposite sides of said transparent or translucent part of said tube.

15. The portable anesthetic delivery device of claim 1 comprising a plurality of sensors for monitoring various operating parameters of said device; said operating parameters being selected from the group consisting of oxygen pressure, oxygen flow rate; nitrous oxide pressure, nitrous oxide flow rate, air pressure, air flow rate, ambient atmospheric pressure, circuit pressure, internal vaporizer temperature, internal vaporizer pressure, gas pressure proximate the common gas port, gas flow rate proximate the common gas port, measure the end-tidal $CO_2$ concentration in an exhalation branch of a breathing circuit, $O_2$ concentration in the inhalation branch of a breathing circuit, and combinations thereof.

16. The portable anesthetic delivery device of claim 15 comprising a monitor; said operating parameters or selected sets of said operating parameters being displayed on said monitor.

17. The portable anesthetic delivery device of claim 16 including connectors adapted to receive inputs from patient monitoring equipment which monitor selected patient parameters; said patient parameters or selected sets thereof being displayed on said monitor.

18. The portable anesthetic delivery device of claim 15 including a controller; said gas flow path further including a by-pass line having an inlet on one side of said vaporizer and an outlet on another side of vaporizer such that at least a portion of carrier gas can by-pass said vaporizer; said flow path further including a by-pass valve which is operable to adjust the ratio of carrier gas which passes through said by-pass line; said controller controlling the by-pass valve to adjust the amount of carrier gas ratio between the carrier gas which enters the vaporizer and the amount of carrier gas which flows through the by-pass line in order to maintain the partial pressure of the anesthetic agent entrained in the carrier gas at a generally constant value.

19. The portable anesthetic delivery device of claim 18 including a temperature controlling device proximate said vaporizer; said temperature controlling device being in communication with and being controlled by said controller; said controller controlling said temperature controlling device in response to a signal received from the internal vaporizer temperature sensor to maintain the internal vaporizer temperature substantially at a desired set point.

20. The portable anesthetic delivery device of claim 19 wherein said temperature controlling device is a thermoelectric heat pump.

21. The portable anesthetic delivery device of claim 19 wherein said controller controls said temperature control device in response to the ambient atmospheric pressure and the internal vaporizer pressure in addition to the internal vaporizer temperature.

22. An anesthetic delivery device comprising:
a vaporizer having an inlet and an outlet;
a gas flow path comprising gas inlets connectable to sources of air, oxygen and nitrous oxide; a manifold in which said air, oxygen and nitrous oxide are combined to form a carrier gas; said vaporizer; a first carrier gas line extending from said manifold to said vaporizer inlet; a second carrier gas line extending from said vaporizer outlet to a common gas port; a by-pass line being connected at a first end to said carrier gas first line and at a second end to said carrier gas second line; a by-pass valve operable to adjust the amount of carrier gas which passes through said by-pass line; and
sensors for monitoring one or more operating parameters of said device; said operating parameters being selected from the group consisting of oxygen pressure, oxygen flow rate; nitrous oxide pressure, nitrous oxide flow rate, air pressure, air flow rate, ambient atmospheric pressure, circuit pressure, internal vaporizer temperature, internal vaporizer pressure, gas pressure proximate the common gas port, gas flow rate proximate the common gas port, measure the end-tidal $CO_2$ concentration in an exhalation branch of a breathing circuit, $O_2$ concentration in the inhalation branch of a breathing circuit, and combinations thereof;

a controller; said controller receiving signals from said sensors indicative of the parameter being monitored and said controller being in operatively connected to said by-pass valve;

said controller controlling said by-pass valve in response to the internal vaporizer pressure and internal vaporizer temperature to maintain the partial pressure of anesthetic agent in the carrier gas at a substantially constant value.

23. The device of claim 22 wherein the vaporizer comprises inner and outer chambers defining vaporizer gas paths, said vaporizer gas paths comprising a first vaporizer path through said inner chamber to said vaporizer exit, and a second vaporizer gas path through said outer chamber to said vaporizer exit; said vaporizer further including a regulator which controls the percentage of gas passing through the vaporizer first gas path; so that the anesthetically saturated gas emanating from the inner chamber combines with the by-pass gas from said vaporizer second flow path.

24. The anesthetic delivery device of claim 22 including a temperature controlling device proximate said vaporizer; said temperature controlling device being in communication with and being controlled by said controller; said controller controlling said temperature controlling device in response to a signal received from the internal vaporizer temperature sensor to maintain the internal vaporizer temperature substantially at a desired set point.

25. The portable anesthetic delivery device of claim 24 wherein said temperature controlling device is a thermoelectric heat pump.

* * * * *